United States Patent
McIver et al.

(10) Patent No.: US 6,307,049 B1
(45) Date of Patent: Oct. 23, 2001

(54) HETEROCYCLIC 2-SUBSTITUTED KETOAMIDES

(75) Inventors: John McMillan McIver; Charles Raymond Degenhardt, both of Cincinnati, OH (US); David Joseph Eickhoff, Edgewood, KY (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/400,681

(22) Filed: Sep. 21, 1999

Related U.S. Application Data
(60) Provisional application No. 60/102,449, filed on Sep. 30, 1998.

(51) Int. Cl.[7] ............... A61K 31/47; A61K 31/445; C07D 217/24; C07D 215/12; C07D 211/32
(52) U.S. Cl. ............. 546/146; 546/168; 546/169; 546/225; 546/226; 546/245; 514/307; 514/311; 514/315; 514/330
(58) Field of Search .................. 546/245, 226, 546/225, 146, 168, 169; 514/307, 311, 330, 315

(56) References Cited

U.S. PATENT DOCUMENTS

| | | | |
|---|---|---|---|
| 4,070,361 | 1/1978 | Petrillo, Jr. | 260/293.85 |
| 5,037,819 | 8/1991 | Han | 514/210 |
| 5,158,959 | 10/1992 | Geiger et al. | 514/307 |
| 5,162,362 | 11/1992 | Geiger et al. | 514/414 |
| 5,192,773 | 3/1993 | Armistead et al. | 514/315 |
| 5,294,603 | 3/1994 | Rinehart | 514/10 |

(List continued on next page.)

FOREIGN PATENT DOCUMENTS

| | | | |
|---|---|---|---|
| 0 196 841 | 10/1986 | (EP) | C07K/5/06 |
| 0 251 164 | 1/1988 | (EP) | C07F/9/65 |
| 0 260 118 | 3/1988 | (EP) | C07C/129/12 |
| 0 423 714 A2 | 4/1991 | (EP) | A61K/7/06 |
| 0 443 132 | 8/1991 | (EP) | C07K/5/06 |
| 0 564 924 | 10/1993 | (EP) | C07K/5/06 |
| 0 610 744 | 8/1994 | (EP) | C07K/5/02 |
| 0 610 745 | 8/1994 | (EP) | C07D/207/16 |
| 0 626 385 | 11/1994 | (EP) | C07D/498/18 |
| 0 947 506 A1 | 10/1999 | (EP) | C07D/209/52 |
| 6 3054 360 | 8/1988 | (JP) | C07D/209/08 |
| 6-256317 | 9/1994 | (JP) | C07D/235/08 |
| WO 92/195933 | 11/1992 | (WO) | C07D/207/16 |
| WO 92/21313 | 12/1992 | (WO) . | |
| WO 94/07858 | 4/1994 | (WO) | C07D/211/60 |
| WO 95/06031 | 8/1994 | (WO) | C07C/317/44 |

(List continued on next page.)

OTHER PUBLICATIONS

Chemical Abstracts, Columbus, OH, vol. 123, No. 15, Oct. 9, 1995 XP–002127159, JP 06–256317.

Spencer, Wandless, Schreiber, Crabtree *Controlling Signal Transduction with Synthetic Ligands*, Science, vol. 262, Nov. 12, 1993, pp. 1019–1024.

Keenan, Yaeger, Courage, Rollins, Pavone, Rivera, Yang, Guo, Amara, Clackson, Gilman, Holt—Ariad Gene Therapeutics, Cambridge, MA *Synthesis and Activity of Bilalent FKBP12 Ligands for the Regulated Dimerization of Proteins* Bioorganics & Medicinal Chemistry 6 (1998) pp. 1309–1335.

Marshall, Schlaf, Csernansky—Dept. Of Chemistry, Northwestern Univ., Evanston, IL *A Convenient Synthesis of Diketopiperazines via Aminolysis of N–Pyruvyl α–Amino Esters* Synthetic Communications, 5(3), (1975) pp. 237–244.

Kim, Kim—Dept. Of Chemistry, Korea Advanced Inst. of Science and Technology, Taejon, Korea *Highly Stereoselective Allylation to Chiral α–Keto Amides Derived From (S)–Indoline–2–carboxylic Acid, Asymmetric Synthesis of Functionalized Tertiary Homoallyl Alcohols* Tetrahedron Letters, vol. 36, No. 38, pp. 6895–6898, 1995, Elsevier Science Ltd.

Slee, Laslo, Elder, Ollmann, Gustchina, Kervinen, Zdanov, Wlodawer, Wong *Selectivity in the Inhibition of HIV and FIV Protease: Inhibitory and Mechanistic Studies of Pyrrolidine–Containing α–Keto Amide and Hydroxyethylamine Core Structures* J. Am. Chem. Soc 1995, 117, pp. 11867–11878.

Ottenheijm, Herscheid, Kerkhoff, Spande—Dept. Or Organic Chemistry, Catholic Univ. Of Nijmegen, The Netherlands *Approaches to Analogues of Dehydrogliotoxin. An Efficient Synthesis of a Gliotoxin Analogue with Anti–Reverse Transcriptease Activity* J. Org. Chem., vol. 41, No. 21, 1976, pp. 3433–3438.

(List continued on next page.)

*Primary Examiner*—D. Margaret Seaman
(74) *Attorney, Agent, or Firm*—Catherine U. Brown; Len W. Lewis; Kelly L. McDow-Dunham

(57) ABSTRACT

The present disclosure describes novel compounds and compositions which are particularly useful for treating hair loss in mammals, including arresting and/or reversing hair loss and promoting hair growth. The present compounds and compositions may also be useful against a variety of disorders including, for example, multi-drug resistance, human immunodeficiency virus (HIV), cardiac injury, and neurological disorders, and may be useful for controlling parasites and invoking immunosuppression.

11 Claims, No Drawings

U.S. PATENT DOCUMENTS

| | | | |
|---|---|---|---|
| 5,330,993 | 7/1994 | Armistead et al. | 514/330 |
| 5,338,755 | 8/1994 | Wagnon et al. | 514/414 |
| 5,385,907 | 1/1995 | Asakura et al. | 514/291 |
| 5,385,918 | 1/1995 | Connell et al. | 514/330 |
| 5,401,766 | 3/1995 | Geiger et al. | 514/307 |
| 5,516,797 | 5/1996 | Armistead et al. | 514/548 |
| 5,543,423 | 8/1996 | Zelle et al. | 514/332 |
| 5,610,165 | 3/1997 | MacCross et al. | 514/315 |
| 5,614,547 | 3/1997 | Hamilton et al. | 514/423 |
| 5,620,971 | 4/1997 | Armistead et al. | 514/212 |
| 5,622,970 | 4/1997 | Armistead et al. | 514/315 |
| 5,633,277 | 5/1997 | Connell et al. | 514/428 |
| 5,665,774 | 9/1997 | Armistead et al. | 514/533 |
| 5,670,504 | 9/1997 | Bochis et al. | 514/247 |
| 5,686,424 | 11/1997 | Connell et al. | 514/19 |
| 5,686,469 | 11/1997 | Connell et al. | 514/330 |
| 5,696,135 | 12/1997 | Steiner et al. | 514/317 |
| 5,721,256 | 2/1998 | Hamilton et al. | 514/330 |
| 5,723,459 | 3/1998 | Armistead et al. | 514/237.8 |
| 5,726,184 | 3/1998 | Zelle | 514/314 |
| 5,744,485 | 4/1998 | Zelle et al. | 514/318 |
| 5,798,355 | 8/1998 | Steiner et al. | 514/248 |
| 5,801,187 | 9/1998 | Li et al. | 514/365 |
| 5,801,197 | 9/1998 | Steiner et al. | 514/548 |
| 5,811,434 | 9/1998 | Zelle et al. | 514/307 |
| 5,859,031 | 1/1999 | Hamilton et al. | 514/343 |

FOREIGN PATENT DOCUMENTS

| | | | |
|---|---|---|---|
| WO 95/26337 | 10/1995 | (WO) | C07D/211/60 |
| WO 96/15101 | 5/1996 | (WO) | C07C/237/02 |
| WO 96/36630 | 11/1996 | (WO) | C07D/401/12 |
| WO 96/40140 | 12/1996 | (WO) | A61K/31/495 |
| WO 96/40633 | 12/1996 | (WO) | C07D/207/16 |
| WO 97/20824 | 12/1996 | (WO) | C07D/241/04 |
| WO 97/07805 | 3/1997 | (WO) | A61K/31/545 |
| WO 97/14439 | 4/1997 | (WO) | A61K/45/06 |
| WO 97/16190 | 5/1997 | (WO) | A61K/31/445 |
| WO 98/50348 | 5/1997 | (WO) | C07C/311/29 |
| WO 97/20815 | 6/1997 | (WO) | C07D/213/28 |
| WO 97/21100 | 6/1997 | (WO) | G01N/33/53 |
| WO 97/21690 | 6/1997 | (WO) | C07D/271/06 |
| WO 98/08815 | 8/1997 | (WO) | C07D/207/48 |
| WO 98/08823 | 8/1997 | (WO) | C07D/239/06 |
| WO 97/31898 | 9/1997 | (WO) | C07D/211/60 |
| WO 97/31899 | 9/1997 | (WO) | C07D/211/60 |
| WO 97/36869 | 10/1997 | (WO) | C07D/211/60 |
| WO 98/22432 | 11/1997 | (WO) | C07C/237/22 |
| WO 98/25580 | 12/1997 | (WO) | A61K/7/06 |
| WO 98/27069 | 12/1997 | (WO) | C07D/241/04 |
| WO 98/13343 | 4/1998 | (WO) | C07D/207/06 |
| WO 98/13355 | 4/1998 | (WO) | C07D/267/02 |
| WO 98/20891 | 5/1998 | (WO) | A61K/38/18 |
| WO 99/62484 | 6/1998 | (WO) | A61K/7/48 |
| WO 99/62490 | 6/1998 | (WO) | A61K/7/48 |
| WO 99/62491 | 6/1998 | (WO) | A61K/7/48 |
| WO 98/06340 | 7/1998 | (WO) | . |
| WO 98/55090 | 12/1998 | (WO) | A61K/7/48 |
| WO 98/55091 | 12/1998 | (WO) | A61K/7/48 |

OTHER PUBLICATIONS

Ottenheijm, Kerkoff, Bejen—Dept. Or Organic Chemistry, Univ. Of Jijmegen, The Netherlands *A Three–step Synthesis of a Gliotoxin Analogue with Anti–reverse Transcriptase Activity* J.C.S. Chem. Comm. 1975, pp. 768–769.

Shuker, Hajduk, Meadows, Fesik *Discovering High–Affinity Ligands for Proteins: SAR by NMR* Science, vol. 274, Nov. 29, 1996, pp. 1531–1534.

Wang, Lane, Resik, Petros, Luly, Krafft—Abbott Laboratories Synthesis and FKBP Binding of Small Molecule Mimics of the Tricarbonyl Region of FK506 *Bioorganic & Medicinal Chemistry Letters,* vol. 4, No. 9, pp. 1161–1166.

Stocks, Birkinshaw, Teague—Fisons Pharmaceuticals *The Contribution to Binding of the Pyranoside Substituents in the Excised Binding Domain of FK–506* Bioorganic & Medicinal Chemistry Letters, vol. 4, No. 12, pp. 1457–1460.

Teague, Stocks—Fisons Pharmaceuticals *The Affinity of the Excised Binding Domain of FK–506 for the Immunophilin FKBP12* Bioorganic & Medicinal Chemistry Letters, vol. 3, No. 10, pp. 1947–1950.

Wakamiya, Konishi, Chaki, Teshima, Shiba—Dept. Of Chemistry, Osaka Univ., Japan *Chemical Studies on Tuberactinomycin, XIII. Synthesis of DL–Dihydroviomycidine and DL–Viomycidine* Heterocycles, vol. 15, No. 2, 1981, pp. 999–1005.

Nadir, Arora—Dept. of Chemistry, Indian Inst. of Technology, Delhi, India *Reaction of N–arylsulfonylaziridines with Dimethylsulfonium–ethoxycarbonly Methylide: Regio–and Stereo–selective Synthesis of 1–arylsulfonyl–2–ethoxycarbonyl Azetidines* J. Chem. Soc., Perkin Trans. 1995, pp. 2605–2609.

Moree, van der Marel, Liskamp——Dept. of Organic Chemistry, Gorlaeus Laboratories, The Netherlands *Synthesis of Peptidosulfinamides and Peptodosulfonamides: Peptidomimetics Containing the Sulfinamide or Sulfonamide Transition–State Isostere* J. Org. Chem. 1995, 60, pp. 5157–5169.

Armistead, Badia, Deininger, Duffy, Saunders, Tung, Thomson, DeCenzo, Futer, Livingston, Murcko, Yamashita, Navia—Vertex Pharmaceuticals Inc., Cambridge, MA *Design, Synthesis and Struucture of Non–macrocyclic Inhibitors of FKBP12, the Major Binding Protein for the Immunosuppressant FK506* Acta Cryst. (1995) D51, pp. 522–528.

Yamashia, Oh, Yen, Bossard, Berandt, Levy, Newman–Tarr, Badger, Luengo, Holt—SmithKline Beecham Pharmaceuticals, King of Prussia, PA *Design, Synthesis and Evaluation of Dual Domain FKPB Ligands* Bioorganic & Medicinal Chemistry Letters, vol. 4, No. 2, pp. 325–328, 1994.

Luengo, Konialian–Beck, Levy, Brandt, Eggleston, Holt—SmithKline Beecham Pharmaceuticals, King of Prussia, PA *Synthesis and Structure–Activity Relationships of Macrocyclic FKBPLigands* Bioorganic & Medicinal Chemistry Letters, vol. 4, No. 2, pp. 321–324, 1994.

Hauske, Dorff, Julin, DiBrino, Spencer, Williams—Pfizer, Inc.—*Design and Synthesis of Novel FKBP Inhibitors* J. Med. Chem. 1992, 35, pp. 4284–4296.

Hamilton, Huang, Connolly, Ross, Guo, Valentine, Suzdak, Steiner—Guilford Pharmaceuticals, Inc. *FKPB12–Binding Domain Analogues of FK506 Are Potent, Nonimmunosuppressive Neurotrophic Agents In Vitro and Promote Recovery in a Mouse Model of Parkinson's Disease* Bioorganic & Medicinal Chemistry Letters, vol. 7, No. 13, pp. 1783–1790, 1997.

Andrus, Schreiber—Dept. of Chemistry, Harvard Univ., Cambridge, MA *Structure–Based Design of an Acycllic Ligand That Bridges FKBP12 and Calcineurin* J. Am. Chem. Soc., 1993, 115, pp. 10420–10421.

Babine, Bleckman, Littlefield, Parge, Pellitier, Lewis, French, Imbacuan, Katoh, Tatlock, Showalter, Villafranca—Agouron Pharmaceuticals, Inc., San Diego, CA *Design, Synthesis and X–Ray Crystallographic Studies of [7.3.1] and [8.3.1] Macrocyclic FKPB012 Ligands* Bioorganic & Medicinal Chemistry Letters, vol. 6, No. 4, pp. 385–390 1996.

Drogovich, Barker, French, Imbacuan, Kalish, Kissinger, Knighton, Lewis, Moomaw Parge, Pelletier, Prins, Showwalter, Tatlock, Tucker, Villafranca—Agouraon Pharmaceuticals, Inc., San Diego, CA *Structure–Based Design of Novel, Urea–Containgin FKBP 12 Inhibitors* J. Med. Chem., 1996, 39, pp. 1872–1884.

Babine, Bleckman, Kissinger, Showalter, Pelletier, Lewis, Tucker, Moomaw, Parge, Villafranca—Agouraon Pharmaceuticals, Inc., San Diego, CA *Design, Synthesis and X–Ray Crystallographic Studies of Novel FKPB–12 Ligands* Bioorganic & Medicinal Chemistry Letters, vol. 5, No. 15, pp. 1719–1724, 1995.

Andres, Macdonald—Dept. of Chemistry, Univ. of Virginia, Charlotteville, VA—Ocain, Longhi, Wyeth–Averat Reserach *Conformationally Defined Analogs of Prolylamides. Trans–Prolyl Peptidomimetics* J. Org. Chem. 1993, 58, pp. 6609–6613.

Tatlock, Kouish, Parge, Knighton, Showalter, Lewis, French, Villafranca—Agouraon Pharmaceuticals, Inc., San Diego, CA *High–Affinity FKBP12 Ligands Derived from (R)–(–)–Carvone. Synthesis and Evaluation of FK50–6 Pyranose Ring Replacements* Bioorganic & Medicinal Chemistry Letters, vol. 5, No. 21, pp. 2489–2494, 1995.

Holt, Konialian–Beck, Oh, Yen, Rozamus, Krog, Erhard, Ortiz, Levy, Brandt, Bossard, Luengo—SmithKline Beecham Pharmaceuticals, King of Prussia, PA Structure–Activity Studies of Synthetic FKPB Ligands as Peptidly–Prolyl Isomerase Inhibitors *Bioorganic & Medicinal Chemistry Letters,* vol. 4, No. 2, pp. 315–320, 1994.

Holt, Luengo, Yamashita, Oh, Konialian, Yen, Rozamus, Brandt, Bossard, Levy, Eggleston, Liang, Schultz, Stout, Clardy, SmithKline Beecham Pharmaceuticals, King of Prussia, PA *Design, Synthesis and Kinetic Evlauation of High–Affinity FKBP Ligands and the X–Ray Crystal Structures of Their Complexes with FKBP12* J. Am. Chem. Soc., 1993, 115, pp. 9925–9938.

Chemical Abstracts 121:224, abstract by Holt, Bioorg Med Chem Lett, 4(2), 315–320, 1994.*

USPatFull2000:31444, abstract of Armistead, US Patent #6,037,370, 2000.*

USPatfull 2000:15654, abstract of Steiner, #6022878, 2000.*

Uspatfull 1999:167033, abstract of Steiner, #6004993, 1999.*

Uspatfull 1999:151234, abstract of Hamilton, #5990131, 1999.*

Uspatfull #1999:128588, abstract of Broder, #5968972, 1999.

USPatFull 1999:106615, abstract of Arzeno, #5948939, 1999.

USPatFull 1999:102830, abstract of steiner, #5,945,441, 1999.

USPatFull 1999:92670, abstract of Armistead, #5,935,954, 1999.

USPatFull 1998:154288, abstract of Steiner, #5,846,981, 1998.*

USPatFull 1998:115749, abstract os Zelle, #5,811,434, 1998.*

USPatFull 1998:104767, abstract of Steiner, #5,801,197, 1998.*

USPatFull 1998:101646, abstract of Steiner, #5,798,355, 1998.*

USPatFull 1998:88862, abstract of Hamilton, #5,786,378, 1998.*

Chemical Abstracts 127:81793, abstract of Wong, WO 9721100, 1997.*

* cited by examiner

US 6,307,049 B1

HETEROCYCLIC 2-SUBSTITUTED KETOAMIDES

CROSS REFERENCE

This application claims priority under Title 35, United States Code §119(e) from Provisional Application Ser. No. 60/102,449, filed Sep. 30, 1998.

FIELD OF THE INVENTION

The present invention relates to novel compounds and compositions which are particularly useful for treating hair loss in mammals, including arresting and/or reversing hair loss and promoting hair growth. The present compounds and compositions may also be useful against a variety of disorders including, for example, multi-drug resistance, human immunodeficiency virus (HIV), cardiac injury, and neurological disorders, and may be useful for controlling parasites and invoking immunosuppression.

BACKGROUND OF THE INVENTION

Hair loss is a common problem which occurs, for example, through natural processes or is often chemically promoted through the use of certain therapeutic drugs designed to alleviate conditions such as cancer. Often such hair loss is accompanied by lack of hair regrowth which causes partial or full baldness. Such baldness is cosmetically unappealing, and is particularly distressing to the person experiencing the hair loss.

As is well-known in the art, hair growth occurs by a cycle of activity which involves alternating periods of growth and rest. This cycle is often divided into three main stages which are known as anagen, catagen, and telogen. Anagen is the growth phase of the cycle and may be characterized by penetration of the hair follicle deep into the dermis with rapid proliferation of cells which are differentiating to form hair. The next phase is catagen, which is a transitional stage marked by the cessation of cell division, and during which the hair follicle regresses through the dermis and hair growth is ceased. The next phase, telogen, is often characterized as the resting stage during which the regressed follicle contains a germ with tightly packed dermal papilla cells. At telogen, the initiation of a new anagen phase is caused by rapid cell proliferation in the germ, expansion of the dermal papilla, and elaboration of basement membrane components. This cycle is repeated throughout hair growth. Wherein hair growth ceases, most of the hair follicles reside in telogen and anagen is not engaged, thus causing the onset of full or partial baldness.

There have been many attempts in the literature to invoke the regrowth of hair by, for example, the promotion or prolongation of anagen. Currently, there are two drugs approved by the United States Food and Drug Administration for the treatment of male pattern baldness: topical minoxidil (marketed as Rogaine® by Pharmacia & Upjohn), and oral finasteride (marketed as Propecia® by Merck & Co., Inc.).

There are conflicting reports, however, regarding the ability of minoxidil to grow hair. In fact, early clinical studies investigating decreased blood pressure via the use of minoxidil did not even mention hypertrichosis (hair growth) as a side effect. See Dormois et al., "Minoxidil in Severe Hypertension: Value When Conventional Drugs Have Failed", *American Heart Journal*, Vol. 90, pp. 360–368 (1975). Indeed, the manufacturers of minoxidil have reported only limited hair growth in a portion of patients using minoxidil. See, e.g., *Physician's Desk Reference®*, 49$^{th}$ Ed. (1995), p. 2580. Furthermore, serious side effects of minoxidil are possible, including vasodilation (which leads to retention of fluid around the heart and increased heart rate), difficulty in breathing, and weight gain. *Physician's Desk Reference®*, 49$^{th}$ Ed. (1995), p. 2581.

Furthermore, while early indicators show that Propecia® may be more effective than Rogaine®, patients using Propecia® are experiencing limited hair growth. See *The New England Journal of Medicine*, Vol. 338, No. 9, Feb. 26, 1998. Furthermore, potential side effects of Propecia® are serious. Propecia® may cause impotence, decreased sexual drive, decreased volume of ejaculate, breast tenderness and enlargement, and hypersensitivity reactions, including lip swelling and skin rash. Furthermore, Propecia® is not indicated for women and children. In fact, women who are pregnant or potentially pregnant should not even handle crushed or broken tablets containing the drug. See *Physician's Desk Reference®*, 52$^{th}$ Ed. (1998), p. 1737 and *The New England Journal of Medicine*, Vol. 338, No. 9, Feb. 26, 1998.

Interestingly, the immunosuppressive agents cyclosporin A and FK506 are known to invoke a prominent hypertrichotic side effect. See Iwabuchi et al., "Effects of Immunosuppressive Peptidyl-Prolyl cis-trans Isomerase (PPIase) Inhibitors, Cyclosporin A, FK506, Ascomycin, and Rapamycin, on Hair Growth Initiation in Mouse: Immunosuppression is not Required for New Hair Growth", *Journal of Dermatological Science*, Vol. 9, pp. 64–69 (1995); Yamamoto et al., "Hair Growth-Stimulating Effects of Cyclosporin A and FK506, Potent Immunosuppressants", *Journal of Dermatological Science*, Vol. 7 (suppl.), pp. S47–S54 (1994); Yamamoto et al., "Stimulation of Hair Growth by Topical Application of FK506, a Potent Immunosuppressive Agent", *Journal of Investigational Dermatology*, Vol. 102, pp. 160–164 (1994); Jiang et al., "Induction of Anagen in Telogen Mouse Skin by Topical Application of FK506, a Potent Immunosuppressant", *Journal of Investigational Dermatology*, Vol. 104, pp. 523–525 (1995); McElwee et al., "Topical FK506: A Potent Immunotherapy for Alopecia Areata? Studies Using the Dundee Experimental Bald Rat Model", *British Journal of Dermatology*, Vol. 137, pp. 491–497 (1997); Maurer et al., "Hair Growth Modulation by Topical Immunophilin Ligands", *American Journal of Pathology*, Vol. 150, No. 4, pp. 1433–1441 (1997); and Paus et al., "Hair Growth Control by Immunosuppression", *Arch. Dermatol. Res.*, Vol. 288, pp. 408–410 (1996). However, use of these compounds as hair growth actives may not be desirable due to their striking potency as immunosuppressive agents.

FK506 is a complex, macrocyclic molecule having the following structure:

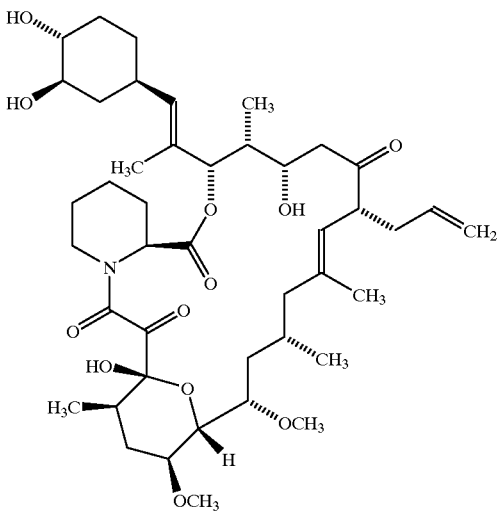

Stocks et al., "The Contribution to Binding of the Pyranoside Substituents in the Excised Binding Domain of FK-506", *Bioorganic & Medicinal Chemistry Letters*, Vol. 4, No. 12, pp. 1457–1460 (1994). Analogs closely resembling this complex macrocycle have been disclosed as having hair growth properties in the form of, for example, alopecia areata and/or male pattern baldness. See. e.g., Kawai et al., U.S. Pat. No. 5,541,193, assigned to Abbott Laboratories, issued Jul. 30, 1996; Asakura et al., U.S. Pat. No. 5,496,564, assigned to Fujisawa Pharmaceutical Co., issued Mar. 5, 1996; Baumann et al., U.S. Pat. No. 5,352,671 assigned to Sandoz Ltd., issued Oct. 4, 1994; and Rupprecht et al., U.S. Pat. No. 5,550,233, assigned to Merck & Co., Inc., issued Aug. 27, 1996.

However, excitement related to the hypertrichotic activities of cyclosporin A and FK506 is somewhat quelled by the lack of reports of hypertrichosis by various smaller, non-macrocyclic immunosuppressive and non-immunosuppressive compounds which are less complex in structure than FK506. See Steiner et al., WO 96/40140, assigned to Guilford Pharmaceuticals, Inc., published Dec. 19, 1996; Hamilton et al., WO 96/40633, assigned to Guilford Pharmaceuticals, Inc., published Dec. 19, 1996; Steiner et al., U.S. Pat. No. 5,696,135, assigned to GPI NIL Holdings, Inc., issued Dec. 9, 1997; Hamilton et al., U.S. Pat. No. 5,614,547, assigned to Guilford Pharmaceuticals, Inc., issued Mar. 25, 1997; Steiner et al., WO 97/16190, assigned to Guilford Pharmaceuticals, Inc., published May 9, 1997; Zelle et al., WO 96/36630, assigned to Vertex Pharmaceuticals, Inc., published Nov. 21, 1996; Armistead et al., WO 97/36869, assigned to Vertex Pharmaceuticals, Inc., published Oct. 9, 1997; Zelle et al., WO 96/15101, assigned to Vertex Pharmaceuticals, Inc., published May 23, 1996; Armistead et al., WO 92/19593, assigned to Vertex Pharmaceuticals, Inc., published Nov. 12, 1992; Armistead et al., WO 94/07858, assigned to Vertex Pharmaceuticals, Inc., published Apr. 14, 1994; Zelle et al., WO 95/26337, assigned to Vertex Pharmaceuticals, Inc., published Oct. 5, 1995; Duffy et al., WO 92/21313, assigned to Vertex Pharmaceuticals, Inc., published Dec. 10, 1992; Armistead et al., U.S. Pat. No. 5,192,773, assigned to Vertex Pharmaceuticals, Inc., issued Mar. 9, 1993; Armistead et al., U.S. Pat. No. 5,330,993, assigned to Vertex Pharmaceuticals, Inc., issued Jul. 19, 1994; Armistead et al., U.S. Pat. No. 5,622,970, assigned to Vertex Pharmaceuticals, Inc., issued Apr. 22, 1997; Armistead et al., U.S. Pat. No. 5,654,332, assigned to Vertex Pharmaceuticals, Inc., issued Aug. 5, 1997; Armistead et al., U.S. Pat. No. 5,620,971, assigned to Vertex Pharmaceuticals, Inc., issued Apr. 15, 1997; Zelle et al., U.S. Pat. No. 5,543,423, assigned to Vertex Pharmaceuticals, Inc., issued Aug. 6, 1996; Armistead et al., U.S. Pat. No. 5,516,797, assigned to Vertex Pharmaceuticals, Inc., issued May 14, 1996; Armistead et al., U.S. Pat. No. 5,665,774, assigned to Vertex Pharmaceuticals, Inc., issued Sep. 9, 1997; Andres et al., "Conformationally Defined Analogs of Prolylamides. trans-Prolyl Peptidomimetics", *Journal of Organic Chemistry*, Vol. 58, pp. 6609–6613 (1993); and Armistead et al., "Design, Synthesis and Structure of Non-macrocyclic Inhibitors of FKBP12, the Major Binding Protein for the Immunosuppressant FK506", *Acta Crystallographica*, D51, pp. 522–528 (1995).

Surprisingly, the present inventors have discovered a novel class of compounds which arrest and/or reverse hair loss or promote hair growth but do not share the complex, macrocyclic structure of FK506. The present inventors have further discovered compounds among this novel class which invoke hair growth yet are surprisingly non-immunosuppressive or are nominally immunosuppressive. The minimized and/or absent immunosuppressive activity of these hypertrichotic compounds are distinct advantages as compared to the immunosuppressive compounds cyclosporin A and FK506.

SUMMARY OF THE INVENTION

The present invention relates to compounds and compositions which are particularly useful for treating hair loss in mammals, including arresting and/or reversing hair loss and promoting hair growth. The present compounds and compositions may also be useful against a variety of disorders including, for example, multi-drug resistance, human immunodeficiency virus (HIV), cardiac injury, and neurological disorders, and are useful for controlling parasites and invoking immunosuppression. The compounds of the present invention have the structure:

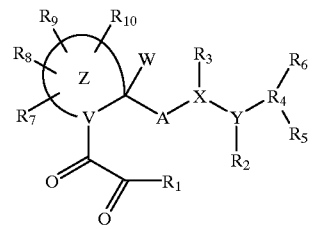

and pharmaceutically acceptable salts, hydrates, and biohydrolyzable amides, esters, and imides thereof, wherein the substituents Z, W, X, Y, V, A, $R_1$, $R_2$, $R_3$, $R_4$, $R_5$, $R_6$, $R_7$, $R_8$, $R_9$, and $R_{10}$ are defined herein.

DETAILED DESCRIPTION OF THE INVENTION

The present invention relates to compounds and compositions which are particularly useful for treating hair loss in mammals, including arresting and / or reversing hair loss and promoting hair growth.

In addition to discovering that the present compounds are useful for treating hair loss, the present inventors have also surprisingly discovered that immunosuppression is not required for hair growth stimulation. The present inventors have further discovered compounds that are useful for treating hair loss but are surprisingly non-immunosuppressive. Preferred compounds of the present invention are therefore, as defined herein, non-immunosuppressive. The present compounds are also useful for treating a variety of other conditions as described herein below.

Publications and patents are referred to throughout this disclosure. All references cited herein are hereby incorporated by reference.

All percentages, ratios, and proportions used herein are by weight unless otherwise specified.

Definition and Usage of Terms

The following is a list of definitions for terms used herein:

As used herein "salt" is a cationic salt formed at any acidic (e.g., carboxyl) group, or an anionic salt formed at any basic (e.g., amino) group. Many such salts are known in the art. Preferred cationic salts include the alkali metal salts (such as, for example, sodium and potassium), alkaline earth metal salts (such as, for example, magnesium and calcium), and organic salts. Preferred anionic salts include the halides (such as, for example, chloride salts). Such acceptable salts must, when administered, be appropriate for mammalian use.

As used herein, "alkenyl" is an unsubstituted or substituted hydrocarbon chain radical having from 2 to about 15 carbon atoms; preferably from 2 to about 10 carbon atoms; more preferably from 2 to about 8 carbon atoms, and most preferably from about 2 to about 6 carbon atoms. Alkenyls have at least one olefinic double bond. Non-limiting examples of alkenyls include vinyl, allyl, and butenyl.

As used herein, "alkoxy" is an oxygen radical having an alkyl, alkenyl, or alkynyl, preferably an alkyl or alkenyl, and most preferably an alkyl substituent. Examples of alkoxy radicals include —O-alkyl and —O-alkenyl. An alkoxy radical may be substituted or unsubstituted.

As used herein, "aryloxy" is an oxygen radical having an aryl substituent. An aryloxy radical may be substituted or unsubstituted.

As used herein, "alkyl" is an unsubstituted or substituted saturated hydrocarbon chain radical having from 1 to about 15 carbon atoms; preferably from 1 to about 10 carbon atoms; more preferably from 1 to about 6 carbon atoms; and most preferably from 1 to about 4 carbon atoms. Preferred alkyls include, for example, methyl, ethyl, propyl, isopropyl, and butyl.

As used herein, "alkylene" refers to an alkyl, alkenyl, or alkynyl which is a diradical. For example, "methylene" is —CH$_2$—. Alkylenes may be substituted or unsubstituted.

As used herein, "aryl" is an aromatic ring radical which is either carbocyclic or heterocyclic. Preferred aryl groups include, for example, phenyl, benzyl, tolyl, xylyl, cumenyl, napthyl, biphenyl, thienyl, furyl, pyrrolyl, pyridinyl, pyrazinyl, thiazolyl, pyrimidinyl, quinolinyl, triazolyl, tetrazolyl, benzothiazolyl, benzofuryl, indolyl, indenyl, azulenyl, fluorenyl, anthracenyl, oxazolyl, isoxazolyl, isotriazolyl, imidazolyl, pyraxolyl, oxadiazolyl, indolizinyl, indolyl, isoindolyl, purinyl, quinolizinyl, quinolinyl, isoquinolinyl, cinnolinyl, and the like. Aryls may be substituted or unsubstituted.

As used herein, "arylalkenyl" is an alkenyl radical substituted with an aryl group or an aryl radical substituted with an alkenyl group. Arylalkenyls may be substituted or unsubstituted.

As used herein, "arylalkyl" is an alkyl radical substituted with an aryl group or an aryl radical substituted with an alkyl group. Preferred arylalkyl groups include benzyl, phenylethyl, and phenylpropyl. Arylalkyls may be substituted or unsubstituted.

As used herein, "biohydrolyzable amides" are amides of the compounds of the present invention which do not interfere with the activity of the compound, or that are readily converted in vivo by a mammalian subject to yield an active compound.

As used herein, "biohydrolyzable esters" are esters of the compounds of the present invention which do not interfere with the activity of the compound, or that are readily converted in vivo by a mammalian subject to yield an active compound.

As used herein, "biohydrolyzable imides" are imides of the compounds of the present invention which do not interfere with the activity of the compound, or that are readily converted in vivo by a mammalian subject to yield an active compound.

As used herein, "carbocyclic ring", "carbocycle", or the like is a hydrocarbon ring radical. Carbocyclic rings are monocyclic or are fused, bridged, or spiro polycyclic rings. Unless otherwise specified, monocyclic rings contain from 3 to about 9 atoms, preferably from about 4 to about 7 atoms, and most preferably 5 or 6 atoms. Polycyclic rings contain from about 7 to about 17 atoms, preferably from about 7 to about 14 atoms, and most preferably 9 or 10 atoms. Carbocyclic rings (carbocycles) may be substituted or unsubstituted.

As used herein, "cycloalkyl" is a saturated carbocyclic or heterocyclic ring radical. Preferred cycloalkyl groups include, for example, cyclobutyl, cyclopentyl, and cyclohexyl. Cycloalkyls may be substituted or unsubstituted.

As used herein, "heteroalkenyl" is an alkenyl radical comprised of carbon atoms and one or more heteroatoms wherein the heteroatoms are selected from the group consisting of oxygen, sulfur, nitrogen, and phosphorous, more preferably, oxygen, sulfur, and nitrogen. Heteroalkenyls may be substituted or unsubstituted.

As used herein, "heteroalkyl" is an alkyl radical comprised of carbon atoms and one or more heteroatoms wherein the heteroatoms are selected from the group consisting of oxygen, sulfur, nitrogen, and phosphorous, more preferably, oxygen, sulfur, and nitrogen. Heteroalkyls may be substituted or unsubstituted.

As used herein, "heteroaryl" is an aryl radical comprised of carbon atoms and one or more heteroatoms wherein the heteroatoms are selected from the group consisting of oxygen, sulfur, nitrogen, and phosphorous, more preferably, oxygen, sulfur, and nitrogen. Heteroaryls may be substituted or unsubstituted.

As used herein, "heteroarylalkenyl" is an arylalkenyl radical wherein the aryl group and/or the alkenyl group is comprised of carbon atoms and one or more heteroatoms wherein the heteroatoms are selected from the group consisting of oxygen, sulfur, nitrogen, and phosphorous, more preferably, oxygen, sulfur, and nitrogen. Heteroarylalkenyls may be substituted or unsubstituted.

As used herein, "heteroarylalkyl" is an arylalkyl radical wherein the aryl group and/or the alkyl group is comprised of carbon atoms and one or more heteroatoms wherein the heteroatoms are selected from the group consisting of oxygen, sulfur, nitrogen, and phosphorous, more preferably, oxygen, sulfur, and nitrogen. Heteroarylalkyls may be substituted or unsubstituted.

As used herein, "heterocyclic ring", "heterocycle", or the like is a ring radical comprised of carbon atoms and one or more heteroatoms in the ring wherein the heteroatoms are selected from the group consisting of oxygen, sulfur, nitrogen, and phosphorous, more preferably, oxygen, sulfur, and nitrogen. Heterocycles are monocyclic or are fused, bridged, or spiro polycyclic rings. Unless otherwise specified, monocycles contain from 3 to about 9 atoms, preferably from about 4 to about 7 atoms, and most preferably 5 or 6 atoms. Polycycles contain from about 7 to about 17 atoms, preferably from about 7 to about 14 atoms, and most preferably 9 or 10 atoms. Heterocyclic rings (heterocycles) may be substituted or unsubstituted.

As used herein, "heterocycloalkyl" is a saturated heterocycle. Heterocycloalkyls may be substituted or unsubstituted.

As used herein, a "lower" moiety (e.g., "lower" alkyl) is moiety having 1 to about 6, preferably 1 to about 4, carbon atoms.

As used herein, "pharmaceutically acceptable" means suitable for use in a human or other mammal.

As used herein, "safe and effective amount of a compound" (or composition, or the like) means an amount that is effective to exhibit biological activity, preferably wherein the biological activity is arresting and/or reversing hair loss or promoting hair growth, at the site(s) of activity in a mammalian subject, without undue adverse side effects (such as toxicity, irritation, or allergic response), commensurate with a reasonable benefit/risk ratio when used in the manner of this invention.

As used herein unless otherwise specified, the term "substituted" in reference to a group, moiety, or the like, means having one or more substituent groups each independently selected from hydrogen, alkyl, alkenyl, alkoxy, hydroxy, oxo, nitro, amino, alkylamino, cyano, halo, carboxy, alkoxyacyl (e.g., carboethyoxy), thiol, aryl, cycloalkyl, heteroaryl, heterocycloalkyl (e.g., piperidinyl, morpholinyl, pyrrolidinyl), imino, thioxo, hydroxyalkyl, aryloxy, and arylalkyl, preferably hydrogen, alkyl, alkenyl, alkoxy, hydroxy, oxo, nitro, amino, alkylamino, halo, thiol, and aryloxy, more preferably hydrogen, alkyl, alkenyl, alkoxy, hydroxy, nitro, amino, alkylamino, and halo, even more preferably hydrogen, alkyl, and alkoxy, and most preferably alkoxy.

As used herein, the term "unsubstituted" includes substitution by a hydrogen moiety. However, a group may alternatively be consistently described as being "substituted" wherein the substitution is with a hydrogen moiety.

As used herein, wherein any variable, moiety, group, or the like occurs more than one time in any variable or structure, its definition at each occurrence is independent of its definition at every other occurrence.

Compounds of the Present Invention

The compounds of the present invention have the structure:

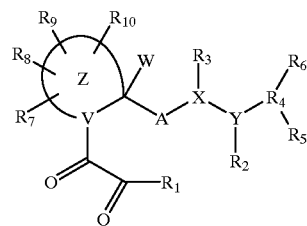

and pharmaceutically acceptable salts, hydrates, and biohydrolyzable amides, esters, and imides thereof, wherein:
(a) V is a heteroatom wherein the heteroatom is nitrogen;
(b) $R_1$ is selected from alkyl having at least 3 carbon atoms, alkenyl, heteroalkyl, heteroalkenyl, cycloalkyl, heterocycloalkyl, aryl, arylalkyl, heteroarylalkyl, arylalkenyl, and heteroarylalkenyl;
(c) Z is a saturated or unsaturated 4-, 5-, 6-, 7-, 8-, or 9-membered heterocycle optionally containing one or more additional heteroatoms selected from O, N, S, S(O), S(O)$_2$, and P((O)OK);
(d) K is selected from hydrogen, alkyl, alkenyl, heteroalkyl, heteroalkenyl, cycloalkyl, heterocycloalkyl, aryl, arylalkyl, heteroarylalkyl, arylalkenyl, and heteroarylalkenyl;
(e) W is selected from nil, hydrogen, and lower alkyl;
(f) A is selected from nil and alkyl;
(g) X and Y are each, independently, selected from C(O), P(O), N, O, and S, wherein:
   (i) when X is C(O) then $R_3$ is nil and Y is selected from N, O, and S;
   (ii) when X is P(O) then $R_3$ is nil and Y is selected from the group consisting of N and O;
   (iii) when X is N then $R_3$ is selected from hydrogen, alkyl, and arylalkyl, Y is C(O), and $R_2$ is nil;
   (iv) when X is O then $R_3$ is nil, Y is C(O), and $R_2$ is nil; and
   (v) when X is S then $R_3$ is nil, Y is C(O), and $R_2$ is nil;
(h) $R_2$ and $R_3$ are each, independently, selected from nil, hydrogen, alkyl, and arylalkyl;
(i) $R_4$ is alkyl;
(j) $R_5$ and $R_6$ are each, independently, selected from nil, hydrogen, alkyl having at least three carbon atoms, alkenyl, heteroalkyl, heteroalkenyl, cycloalkyl, heterocycloalkyl, aryl, arylalkyl, heteroarylalkyl, arylalkenyl, and heteroarylalkenyl, or wherein $R_5$ and $R_6$ are bonded together to form a carbocyclic or hetercyclic ring; wherein at least one of $R_5$ or $R_6$ is not nil or hydrogen; and wherein when A is nil and $R_7$ and $R_8$ are bonded together to form a 5- or 6-membered aromatic carbocyclic ring which is fused to Z, then $R_4$, $R_5$, and $R_6$ are not bonded together to form a substituted or unsubstituted tetrahydronapthalene moiety;
(k) $R_7$, $R_8$, and $R_9$, and $R_{10}$ are each, independently, selected from nil, hydrogen, alkyl, alkenyl, heteroalkyl, heteroalkenyl, cycloalkyl, heterocycloalkyl, aryl, arylalkyl, heteroarylalkyl, arylalkenyl, heteroarylalkenyl, halo, cyano, hydroxy, oxo, imino, —$R_{14}SR_{15}$, —$R_{14}S(O_2)R_{15}$, —$R_{14}S(O)R_{15}$, —$R_{14}C(O)R_{15}$, —$R_{14}C(O)NR_{15}R_{16}$, —$R_{14}C(O)OR_{15}$, —$R_{14}OR_{15}$, —$R_{14}NR_{15}R_{16}$, —$R_{14}P(O)NR_{15}R_{16}$, —$R_{14}P(O)OR_{15}R_{16}$, and a spiro moiety, and wherein $R_7$ and $R_8$ may be optionally bonded together to form an aromatic or saturated, carbocyclic or heterocyclic ring wherein the ring is fused to Z; wherein when A is nil and X is C(O) at least one of $R_7$, $R_8$, $R_9$, and $R_{10}$ is not nil or hydrogen;

(l) $R_{14}$, and $R_{15}$ are each, independently, selected from nil, hydrogen, alkyl, alkenyl, heteroalkyl, heteroalkenyl, cycloalkyl, heterocycloalkyl, aryl, arylalkyl, heteroarylalkyl, arylalkenyl, and heteroarylalkenyl; and (m) $R_{16}$ is selected from hydrogen and alkyl.

The Ring System Z

The present compounds are comprised of a ring system, Z, which is a saturated or unsaturated 4-, 5-, 6-, 7-, 8-, or 9-membered heterocycle. Preferably the Z ring system is a 5-, 6-, or 7-membered heterocycle, more preferably a 5- or 6-membered heterocycle.

At the 1-position of the ring system is the V heteroatom which is a nitrogen atom. The Z ring optionally contains one or more heteroatoms or heteromoieties (herein collectively described as heteroatoms for simplicity) in addition to the V nitrogen wherein the additional heteroatoms are selected from oxygen (O), nitrogen (N), sulfur (S), sulfoxide (S(O)), sulfone (S(O)$_2$), and phosphonate (P((O)OK)). Preferably the additional heteroatoms are selected from the group consisting of O, N, S, S(O), and S(O)$_2$, but more preferably Z does not contain any heteroatoms other than the V nitrogen at the 1-position.

Of course, wherein N is an additional heteroatom, the additional N heteroatom must be substituted, most preferably with hydrogen or alkyl. The S(O), S(O)$_2$, and P(O)OK heteroatoms are depicted below in Table 1 for clarity:

TABLE 1

S(O)

S(O)$_2$

P(O)OK

TABLE 1-continued

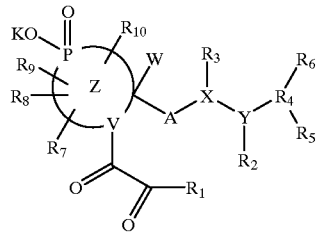

The $R_1$ Moiety

The $R_1$ moiety is attached to the ketoamide moiety and is selected from alkyl having at least 3 carbon atoms, alkenyl, heteroalkyl, heteroalkenyl, cycloalkyl, heterocycloalkyl, aryl, arylalkyl, heteroarylalkyl, arylalkenyl, and heteroarylalkenyl. The $R_1$ moiety is preferably substituted with at least one substituent other than hydrogen. In addition to the substituents defined herein which can substitute all moieties, the substituents oxo, amido, —O-alkyl—C(O)OR$_{32}$, and —O-alkyl-C(O)NHR$_{32}$, wherein $R_{32}$ is selected from hydrogen and alkyl, may also substitute on the $R_1$ moiety.

The $R_1$ moiety is preferably selected from alkyl having at least 3 carbon atoms, heteroalkyl, cycloalkyl, heterocycloalkyl, aryl, arylalkyl, and heteroarylalkyl, even more preferably aryl, arylalkyl, and heteroarylalkyl, most preferably aryl. The most preferred aryl for the $R_1$ moiety is substituted aryl (most preferably substituted phenyl), particularly aryl having at least one alkoxy substituent. Particularly preferred $R_1$ moieties are shown below in Table 2.

TABLE 2

Preferred $R_1$ Moieties

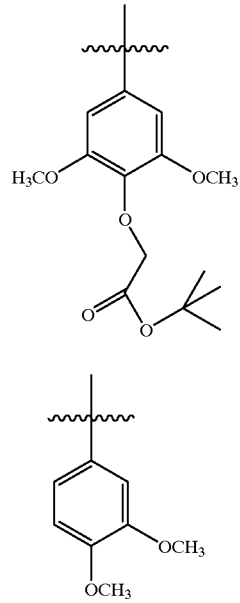

TABLE 2-continued

Preferred $R_1$ Moieties

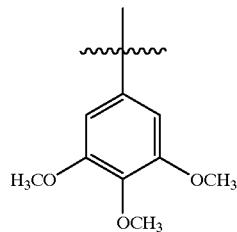

The A—X—Y—$R_4$ Moiety

At the 2-position of the Z ring is the A—X—Y—$R_4$ moiety which is substituted, as described herein, by $R_2$, $R_3$, $R_5$, and $R_6$.

The A moiety of the side chain is selected from nil and alkyl. However, wherein A is nil and X is C(O), at least one of the ring substituents $R_7$, $R_8$, $R_9$, and $R_{10}$ (each of which are described more fully herein below) is not nil or hydrogen. Most preferably, the A moiety is nil, meaning that most preferably, at least one of $R_7$, $R_8$, $R_9$, and $R_{10}$ is not nil or hydrogen. Of course, wherein A is nil, X is directly attached to the Z ring.

The X moiety of the side chain is dependent upon the structure of the Y moiety and vice versa. X and Y are each, independently, selected from C(O) (i.e., carbonyl), N, O, S, with the following limitations:

(i) when X is C(O) then $R_3$ is nil and Y is selected from N, O, and S;

(ii) when X is P(O) then $R_3$ is nil and Y is selected from N and O;

(iii) when X is N then $R_3$ is selected from hydrogen, alkyl, and arylalkyl, Y is selected from C(O) and P(O), and $R_2$ is nil;

(iv) when X is O then $R_3$ is nil, Y is selected from C(O) and P(O), and $R_2$ is nil; and (v) when X is S then $R_3$ is nil, Y is C(O), and $R_2$ is nil;

Preferably, X and Y are each, independently, selected from C(O), N, and O. More preferably, X and Y are each, independently, selected from is C(O) and N.

X and Y are substituted by $R_3$ and $R_2$, respectively. $R_3$ and $R_2$ are each, independently, selected from nil, hydrogen, alkyl, and arylalkyl. Wherein X is O or S, then $R_3$ is nil, and wherein Y is O or S, then $R_2$ is nil. Wherein X is P(O), then $R_3$ is nil, and wherein Y is P(O) then $R_2$ is nil. Wherein X is N, then $R_3$ is selected from hydrogen, alkyl, and arylalkyl, preferably hydrogen and alkyl, most preferably hydrogen. Wherein Y is N, then $R_2$ is selected from hydrogen, alkyl, and arylalkyl, preferably hydrogen and alkyl, most preferably hydrogen.

The $R_4$ moiety is an alkyl moiety. The preferred alkyl moieties follow the preferred limitations set forth above, with the most preferred $R_4$ moiety being a methylene or methyne group (i.e., a $C_1$ moiety bearing only one hydrogen substituent).

The $R_5$ and $R_6$ moieties are each directly attached to $R_4$. $R_5$ and $R_6$ are each, independently, selected from nil, hydrogen, alkyl having at least three carbon atoms, alkenyl, heteroalkyl, heteroalkenyl, cycloalkyl, heterocycloalkyl, aryl, arylalkyl, heteroarylalkyl, arylalkenyl, and heteroarylalkenyl; or wherein $R_5$ and $R_6$ are bonded together to form a carbocyclic or hetercyclic ring; wherein at least one of $R_5$ or $R_6$ is not nil or hydrogen.

Preferably, $R_5$ and $R_6$ are each, independently, selected from nil, hydrogen, alkyl having at least three carbon atoms, alkenyl, heteroalkyl, heteroalkenyl, cycloalkyl, heterocycloalkyl, aryl, arylalkyl, heteroarylalkyl, arylalkenyl, and heteroarylalkenyl; wherein at least one of $R_5$ or $R_6$ is not nil or hydrogen. More preferably, $R_5$ and $R_6$ are each, independently, selected from alkyl having at least three carbon atoms, heteroalkyl, cycloalkyl, heterocycloalkyl, aryl, arylalkyl, and heteroarylalkyl. Most preferably, $R_5$ and $R_6$ are each, independently, arylalkyl. It is often preferred that $R_5$ and $R_6$ are equivalent moieties. Of course, $R_5$ and $R_6$ may be each, independently, substituted. Exemplary $R_5$ and $R_6$ moieties are shown in Table 3 below.

TABLE 3

Exemplary $R_5$ and $R_6$ Moieties

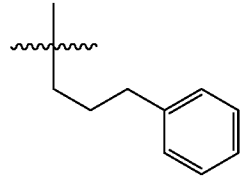
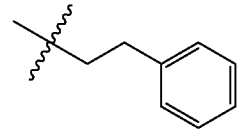
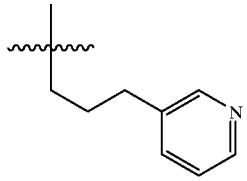
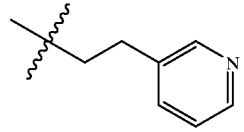

Wherein when A is nil and $R_7$ and $R_8$ are bonded together to form a 5- or 6-membered aromatic carbocyclic ring which is fused to Z, then $R_4$, $R_5$, and $R_6$ are not bonded together to form a substituted or unsubstituted tetrahydronapthalene moiety. As used herein, the substituted or unsubstituted tetrahydronapthalene moiety is defined as:

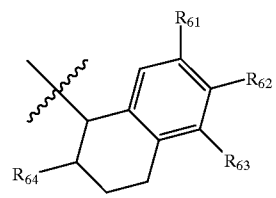

wherein $R_{61}$, $R_{62}$, and $R_{63}$ are each, independently, selected from hydrogen, halogen, alkyl, O-alkyl, $(CH_2)_b$-aryl, and $R_{50}(CH_2)_b$-aryl, wherein $R_{50}$ is selected from O, S, and $NR_{51}$; wherein $R_{51}$ is selected from alkyl and hydrogen; b is an integer from 0 to 4; and $R_{64}$ is selected from hydrogen and $(CH_2)_c$-$R_{52}$, wherein $R_{52}$ is selected from aryl and $NR_{53}R_{54}$, wherein $R_{53}$ and $R_{54}$ are each, independently, selected from hydrogen, alkyl, and $(CH_2)$-aryl, or wherein $R_{53}$ and $R_{54}$ are bonded together to form a 5- or 6-membered heterocyclic ring; and c is an integer from 1 to 3.

The W Moiety

The Z ring may be substituted at the 2-position by an additional moiety, W. The W moiety is selected from nil, hydrogen, and lower alkyl, preferably hydrogen and lower alkyl, most preferably hydrogen. Wherein W is lower alkyl, W is most preferably methyl.

The Z Ring Substituents $R_7$, $R_8$, $R_9$ and $R_{10}$

In addition to the aforementioned substituents at positions 1 and 2 of the Z ring, the Z ring may also have additional substituents at the other available positions, such additional substituents being defined as $R_7$, $R_8$, $R_9$, and $R_{10}$. These substituents $R_7$, $R_8$, and $R_9$, and $R_{10}$ are each, independently, selected from nil, hydrogen, alkyl, alkenyl, heteroalkyl, heteroalkenyl, cycloalkyl, heterocycloalkyl, aryl, arylalkyl, heteroarylalkyl, arylalkenyl, heteroarylalkenyl, halo, cyano, hydroxy, oxo, imino, —$R_{14}SR_{15}$, —$R_{14}S(O_2)R_{15}$, —$R_{14}S(O)R_{15}$, —$R_{14}C(O)R_{15}$, —$R_{14}C(O)NR_{15}R_{16}$, —$R_{14}C(O)OR_{15}$, —$R_{14}OR_{15}$, —$R_{14}NR_{16}$, —$R_{14}P(O)NR_{15}R_{16}$, —$R_{14}P(O)OR_{15}R_{16}$, and a spiro moiety, and wherein $R_7$ and $R_8$ may be optionally bonded together to form an aromatic or saturated, carbocyclic or heterocyclic ring wherein the ring is fused to Z; wherein when A is nil and X is C(O) at least one of $R_7$, $R_8$, $R_9$, and $R_{10}$ is not nil or hydrogen. $R_{14}$, and $R_{15}$ are each, independently, selected from nil, hydrogen, alkyl, alkenyl, heteroalkyl, heteroalkenyl, cycloalkyl, heterocycloalkyl, aryl, arylalkyl, heteroarylalkyl, arylalkenyl, and heteroarylalkenyl. $R_{16}$ is selected from hydrogen and alkyl.

Preferably, $R_7$, $R_8$, and $R_9$, and $R_{10}$ are each, independently, selected from nil, hydrogen, alkyl, heteroalkyl, heteroalkenyl, cycloalkyl, heterocycloalkyl, aryl, arylalkyl, heteroarylalkyl, halo, hydroxy, oxo, —$R_{14}SR_{15}$, —$R_{14}S(O_2)R_{15}$, —$R_{14}S(O)R_{15}$, —$R_{14}C(O)R_{15}$, —$R_{14}C(O)NR_{15}R_{16}$, —$R_{14}OR_{15}$, —$R_{14}NR_{15}R_{16}$, and a spiro moiety, and wherein $R_7$ and $R_8$ may be optionally bonded together to form an aromatic or saturated, carbocyclic or heterocyclic second ring wherein the second ring is fused to Z. More preferably, $R_7$, $R_8$, and $R_9$, and $R_{10}$ are each, independently, selected from nil, hydrogen, alkyl, heteroalkyl, heteroalkenyl, aryl, arylalkyl, heteroarylalkyl, halo, hydroxy, oxo, —$R_{14}SR_{15}$, —$R_{14}S(O_2)R_{15}$, —$R_{14}S(O)R_{15}$, —$R_{14}C(O)R_{15}$, —$R_{14}C(O)NR_{15}R_{16}$, —$R_{14}OR_{15}$, —$R_{14}NR_{15}R_{16}$, and a spiro moiety, and wherein $R_7$ and $R_8$ may be optionally bonded together to form an aromatic or saturated, carbocyclic or heterocyclic second ring wherein the second ring is fused to Z. Even more preferably, $R_7$, $R_8$, and $R_9$, and $R_{10}$ are each, independently, selected from nil, hydrogen, alkyl, heteroalkyl, heteroalkenyl, aryl, arylalkyl, heteroarylalkyl, halo, hydroxy, —$R_{14}C(O)R_{15}$, —$R_{14}C(O)NR_{15}R_{16}$, —$R_{14}OR_{15}$, —$R_{14}NR_{15}R_{16}$, and a spiro moiety, and wherein $R_7$ and $R_8$ may be optionally bonded together to form an aromatic or saturated, carbocyclic or heterocyclic second ring wherein the second ring is fused to Z. Most preferably, $R_7$ and $R_8$ are bonded together to form an aromatic or saturated (preferably aromatic), carbocyclic or heterocyclic (preferably carbocyclic) second ring wherein the second ring is fused to Z.

Wherein $R_7$ and $R_8$ are bonded together to form an aromatic or saturated, carbocyclic or heterocyclic second ring wherein the second ring is fused to Z, the second ring may, of course, be substituted or unsubstituted. A preferred second ring is phenyl.

Preferably, at least one of $R_7$, $R_8$, $R_9$, and $R_{10}$ is not nil or hydrogen. Exemplary compounds of the present invention are presented in the following tables.

TABLE 4

Exemplary Compounds of the Present Invention

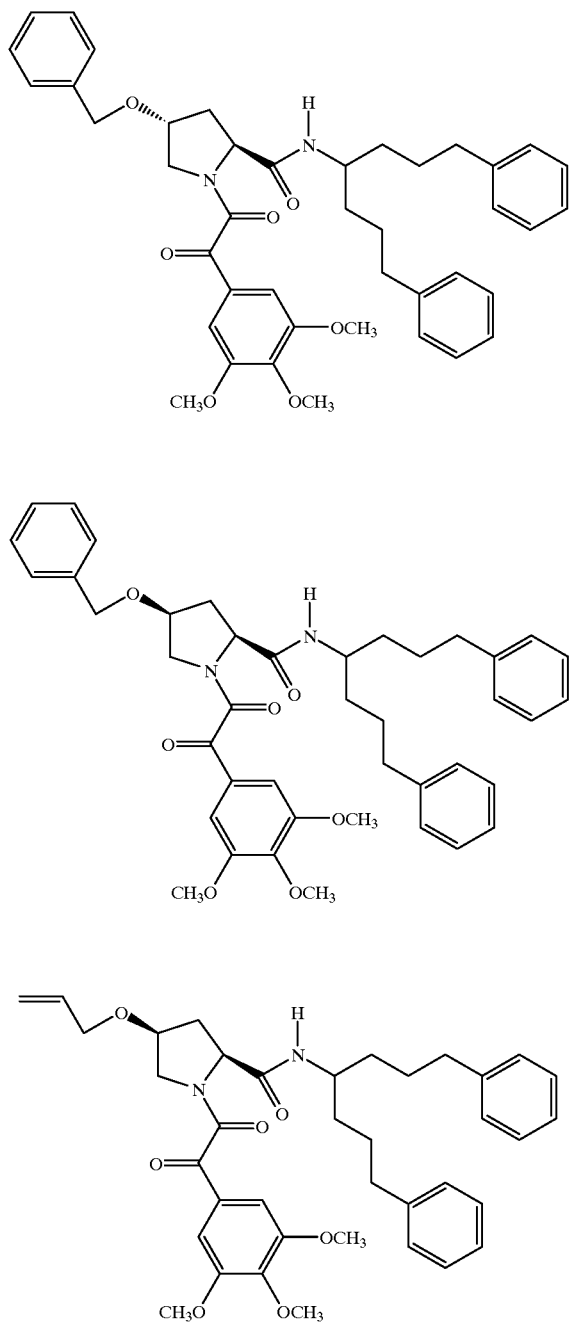

TABLE 4-continued
Exemplary Compounds of the Present Invention
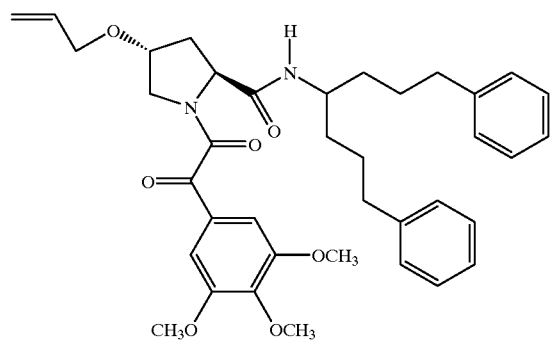
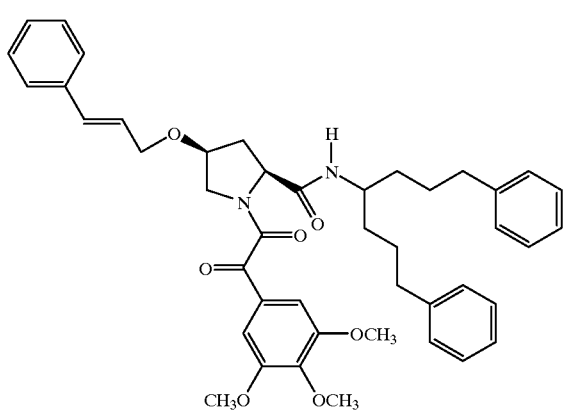
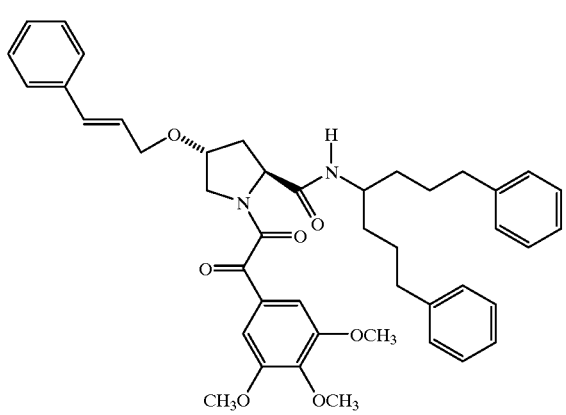
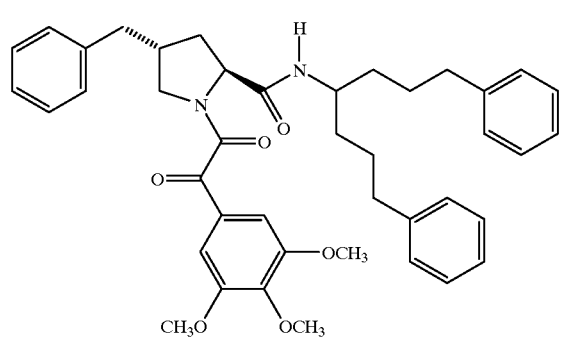
TABLE 4-continued
Exemplary Compounds of the Present Invention
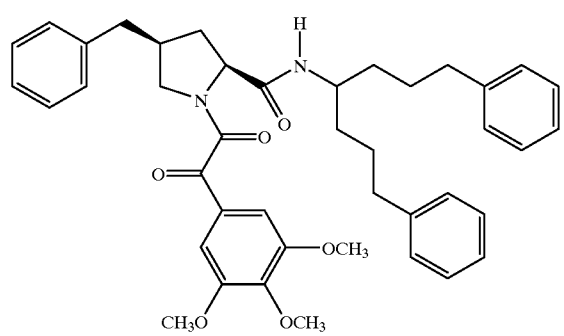
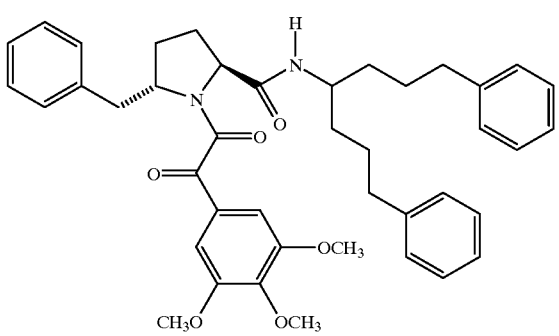
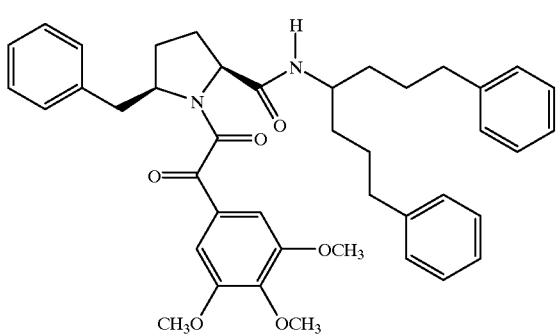
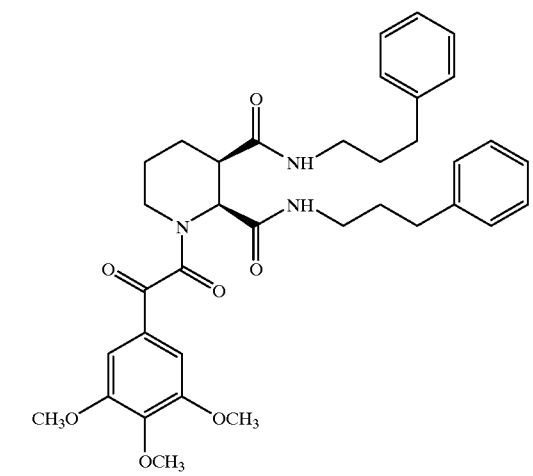

TABLE 4-continued

Exemplary Compounds of the Present Invention

TABLE 5

Exemplary Compounds of the Present Invention

TABLE 5-continued

Exemplary Compounds of the Present Invention

TABLE 5-continued

Exemplary Compounds of the Present Invention

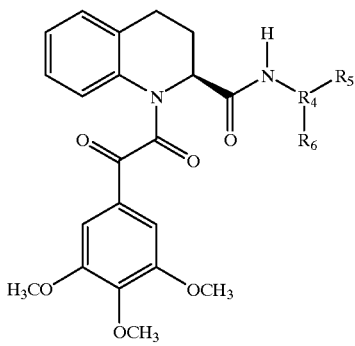

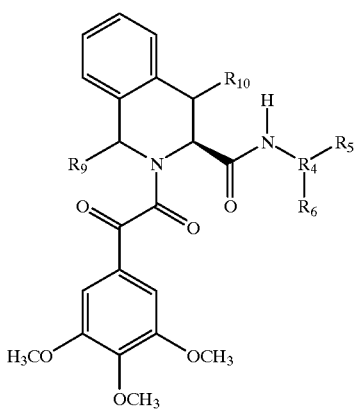

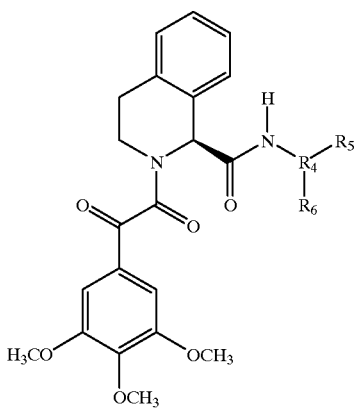

wherein, in Table 5, $R_{18}$, $R_{19}$, and $R_{20}$ are each, independently, selected from hydrogen, alkoxy, aryloxy, hydroxy, nitro, amino, halo, and thiol.

TABLE 6

Exemplary Compounds of the Present Invention

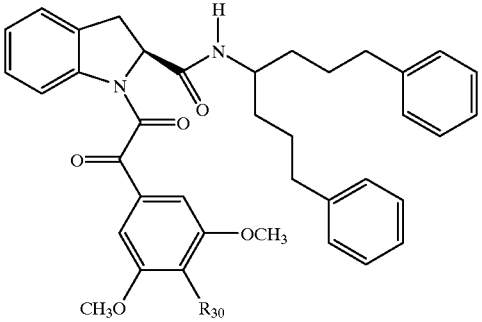

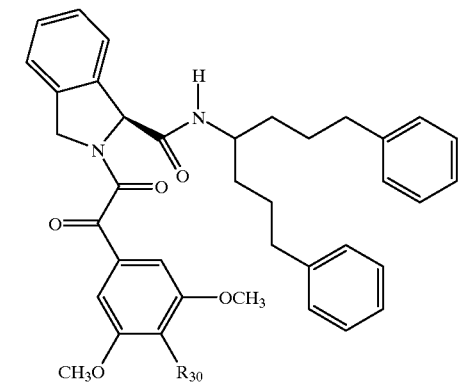

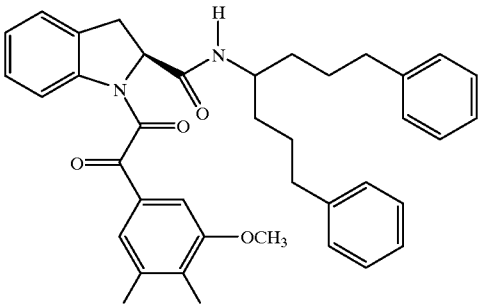

wherein in Table 6, $R_{30}$ is selected from the group consisting of —$OR_{32}$ and —$OCH_2C(O)OR_{32}$, wherein $R_{32}$ is selected from the group consisting of hydrogen and alkyl.

TABLE 7
Exemplary Compounds of the Present Invention
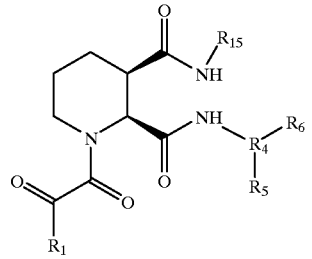
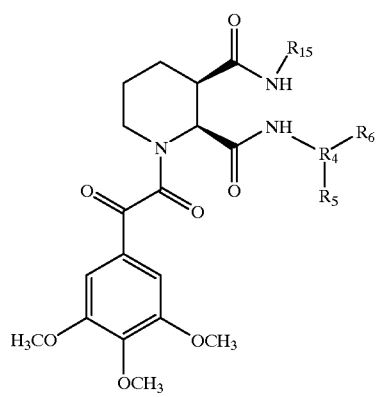
wherein in Table 7, $R_{35}$ is selected from hydrogen and $-OR_{36}$, wherein $R_{36}$ is selected from hydrogen and alkyl.
TABLE 8
Exemplary Compounds of the Present Invention
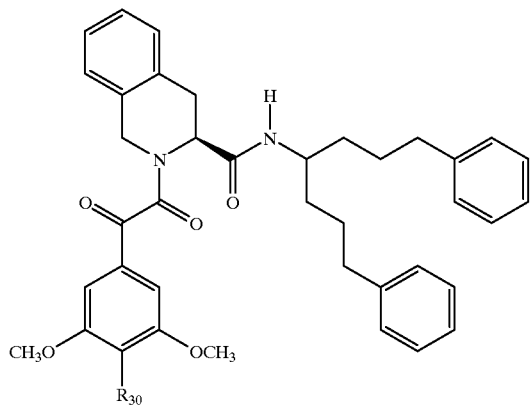
TABLE 8-continued
Exemplary Compounds of the Present Invention
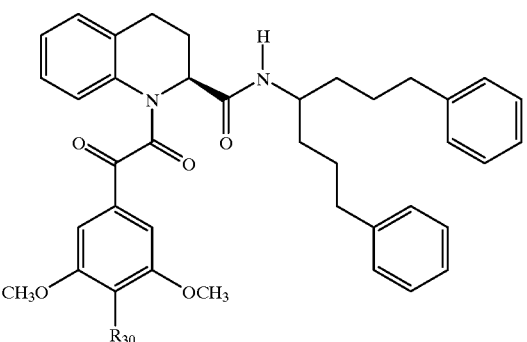
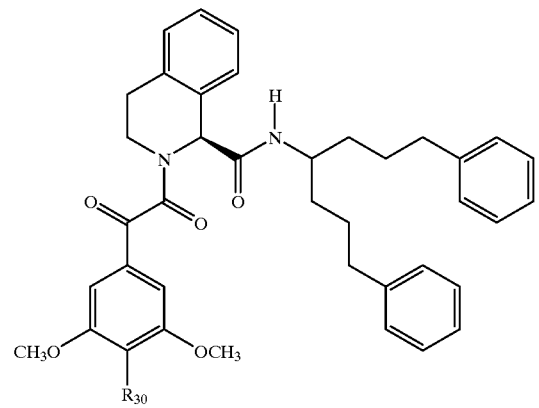
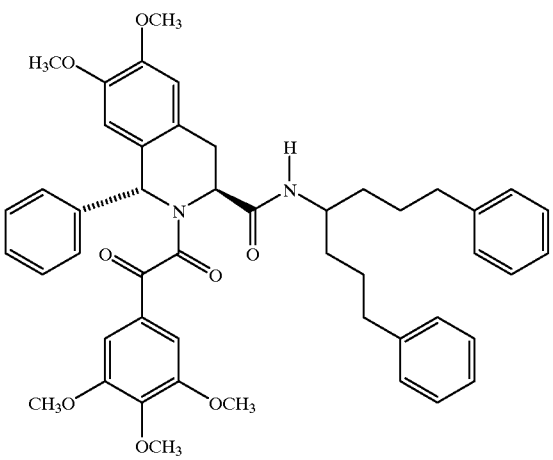
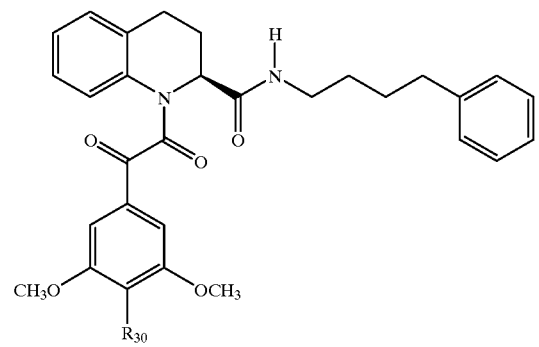

TABLE 8-continued
Exemplary Compounds of the Present Invention
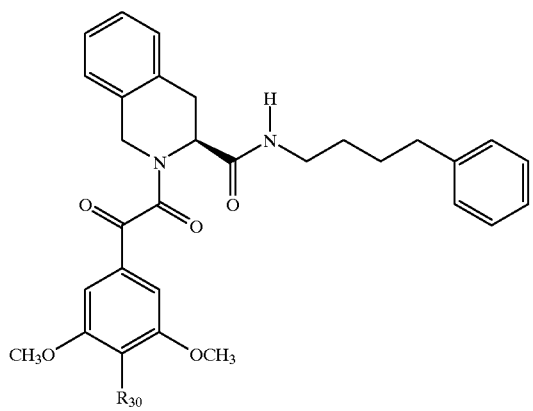
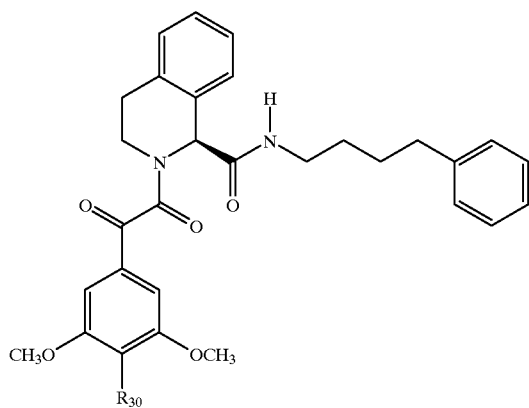
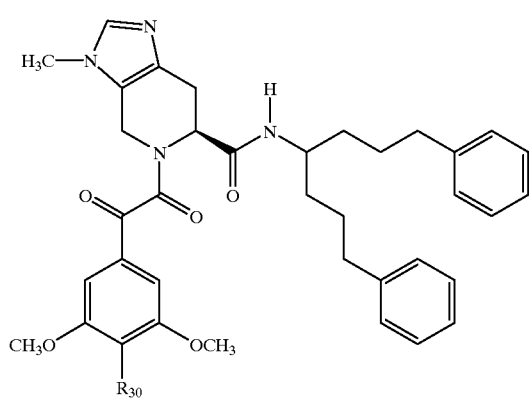
TABLE 8-continued
Exemplary Compounds of the Present Invention
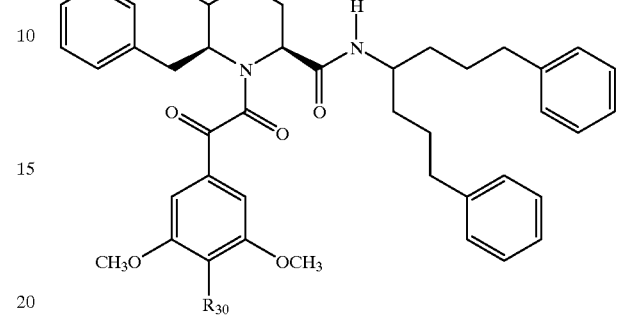
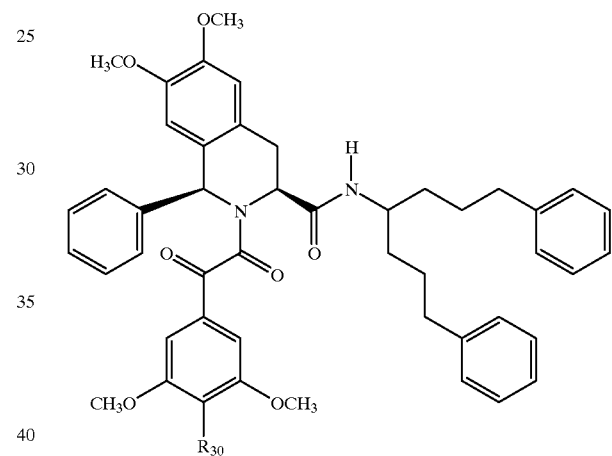
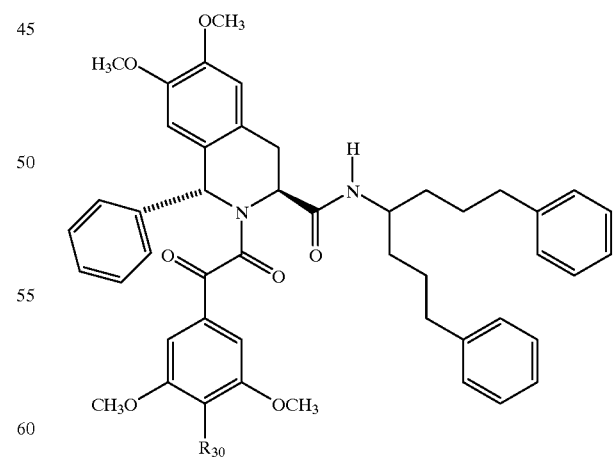

TABLE 8-continued
Exemplary Compounds of the Present Invention
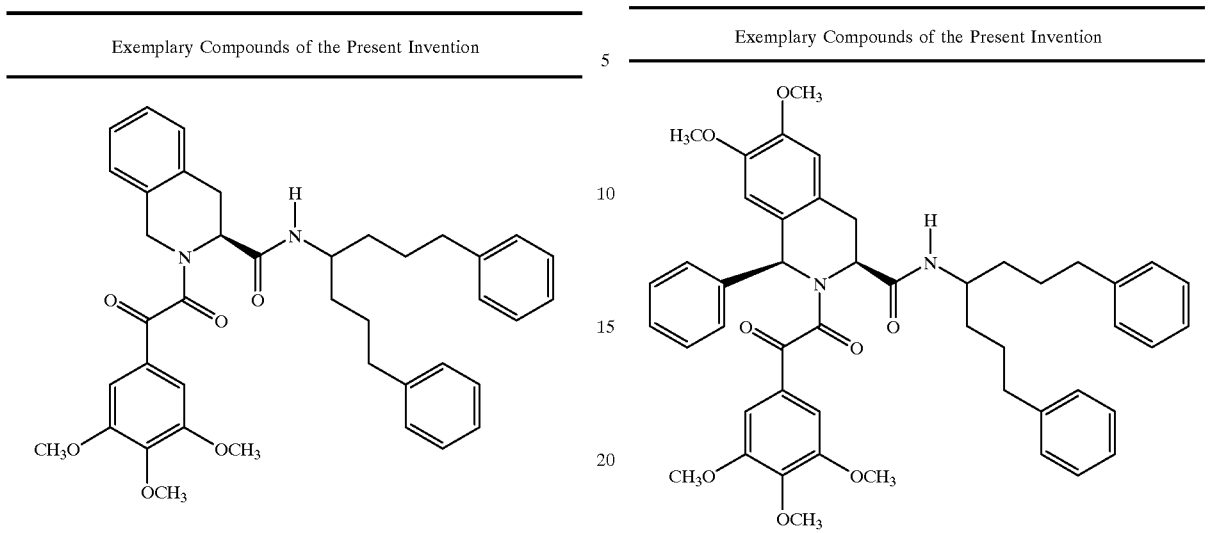
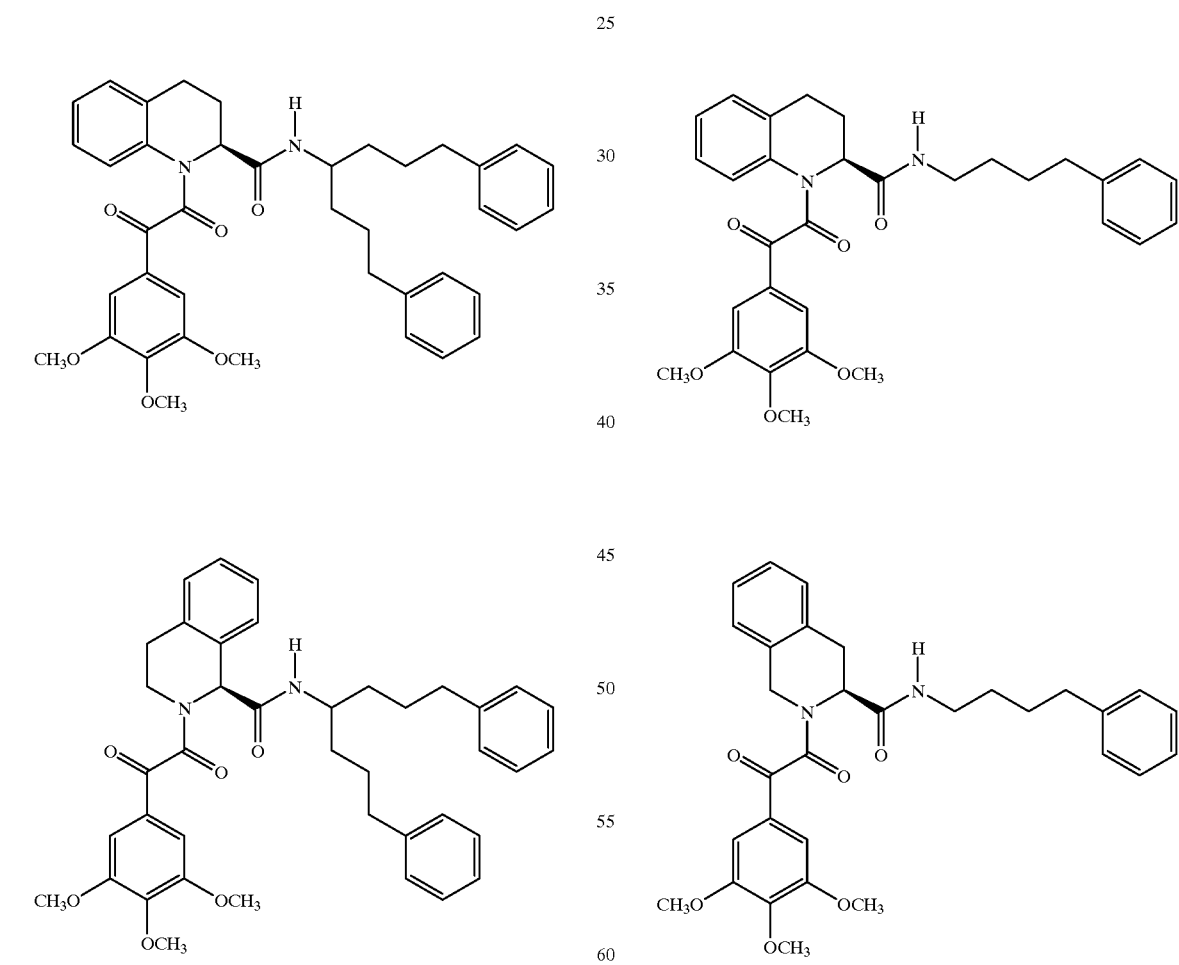

TABLE 8-continued

Exemplary Compounds of the Present Invention

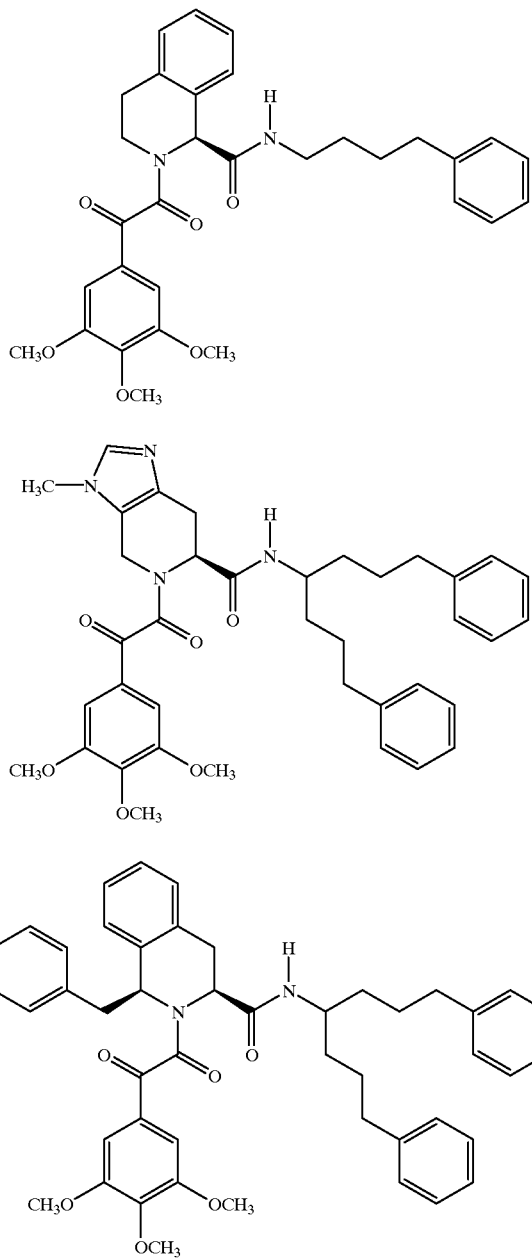

wherein in Table 8, $R_{30}$ is selected from —$OR_{32}$ and —$OCH_2C(O)OR_{32}$, wherein $R_{32}$ is selected from hydrogen and alkyl.

Analytical Methods

The present compounds are hair growth actives, the more preferred among these being non-immunosuppressive. The compounds (test compounds) of the present invention may be tested for their ability to induce anagen and their immunosuppressive activity (or lack thereof) using the following methods. Alternatively, other methods well-known in the art may be used (but with the term "non-immunosuppressive" being defined according to the method disclosed herein).

Telogen Conversion Assay

The Telogen Conversion Assay measures the potential of a test compound to convert mice in the resting stage of the hair growth cycle ("telogen"), to the growth stage of the hair growth cycle ("anagen").

Without intending to be limited by theory, there are three principal phases of the hair growth cycle: anagen, catagen, and telogen. It is believed that there is a longer telogen period in C3H mice (Harlan Sprague Dawley, Inc., Indianapolis, Ind.) from approximately 40 days of age until about 75 days of age, when hair growth is synchronized. It is believed that after 75 days of age, hair growth is no longer synchronized. Wherein about 40 day-old mice with dark fur (brown or black) are used in hair growth experiments, melanogenesis occurs along with hair (fur) growth wherein the topical application of hair growth promoters are evaluated. The Telogen Conversion Assay herein below is used to screen compounds for potential hair growth by measuring melanogenesis.

Three groups of 44 day-old C3H mice are utilized: a vehicle control group, a positive control group, and a test compound group, wherein the test compound group is administered a compound of the present invention. The length of the assay is at least 19 days with 15 treatment days (wherein the treatment days occur Mondays through Fridays). Day 1 is the first day of treatment. Most studies will end on Day 19, but a few may be carried out to Day 24 if the melanogenesis response looks positive, but occurs slowly. A typical study design is shown in Table 9 below:

TABLE 9

| Group # | Animal # | Compound | Concentration | Application volume | Length of Study |
|---|---|---|---|---|---|
| 1 | 1–10 | Test Compound | 5% in vehicle** | 400 µL topical | 19 or 24 days |
| 2 | 11–20 | Cyclosporin A | 0.19% in vehicle** | 400 µL topical | 19 or 24 days |
| 3 | 21–30 | Vehicle** | N/A | 400 µL topical | 19 or 24 days |

**The vehicle is 60% ethanol, 20% propylene glycol, and 20% dimethyl isosorbide (commercially available from Sigma Chemical Co., St. Louis, MO).

The mice are treated topically Monday through Friday on their lower back (base of tail to the lower rib). A pipettor and tip are used to deliver 400 µL to each mouse's back. The 400 µL application is applied slowly while moving hair on the mouse to allow the application to reach the skin.

While each treatment is being applied to the mouse topically, a visual grade of from 0 to 4 will be given to the skin color in the application area of each animal. As the mice convert from telogen to anagen their skin color will become more bluish-black. As indicated in Table 10, the grades 0 to 4 represent the following visual observations as the skin progresses from white to bluish-black:

TABLE 10

| Visual Observation | Grade |
|---|---|
| Whitish Skin Color | 0 |
| Skin is light gray (indication of initiation of anagen) | 1 |
| Appearance of Blue Spots | 2 |
| Blue Spots are aggregating to form one large blue area | 3 |
| Skin is dark blue (almost black) with color covering majority of treatment area (indication of mouse in full anagen) | 4 |

Immunosuppression Assay

The immunosuppression assay herein predicts the immunosuppressive activity of a compound of the present invention. The assay is performed as follows:

Spleens are excised from euthanized ($CO_2$ asphyxiation) adult male C3H mice ranging in age from seven to sixteen weeks old (live mice commercially available from Harlan Sprague Dawley, Inc., Indianapolis, Ind.). The spleens are placed immediately in cold Hanks Balanced Salt Solution (HBSS, commercially available from Gibco-BRL, Gaithersburg, Md.). The spleens are then ground up between frosted glass slides and filtered through a sterile screen to remove tissue debris. The resulting cell suspension is underlayed with an equal volume of Ficoll-Paque Plus (commercially available from Pharmacia Biotech, Piscataway, N.J.) and centrifuged at 400×g for approximately forty minutes at 20° C. in order to collect the splenocytes. The splenocytes are collected from the interface using a disposable pipet and are washed twice with HBSS, followed by centrifugation at 100×g for ten min at 20° C. Splenocytes are resuspended in five to ten mL of cell culture media consisting of phenol red-free RPMI 1640 (culture media commercially available from Gibco-BRL) containing 10% heat-inactivated fetal bovine serum (Gibco-BRL), penicillin (50 U/mL), streptomycin (100 µg/mL), L-glutamine (2 mM), 2-mercaptoethanol ($10^{-5}$ M), and N-2-hydroxyethylpiperazine-N'-2-ethanesulfonic acid (HEPES) (10 mM). The cells are counted and checked for viability using, for example, trypan blue. Splenocytes are resuspended in medium at $10^6$ cells/mL and pipetted into 96 well round bottom plates at $10^5$ cells/well. Splenocytes are activated by addition of 50 µL/well of conconavalin A (final assay concentration=5 µg/ml) in the presence or absence of a test compound. Test compounds are made up as stock solutions in methyl sulfoxide (DMSO), then diluted in medium and 50 µL/well added, such that the final concentration of DMSO in the assay is below 0.05%. The plates are incubated at 37° C. with 5% $CO_2$ for 48 hours. After 48 hours, the cells are pulsed with 1 µCi/well of methyl-$^3$H-thymidine (commercially available from Amersham, Buckinghamshire, England) and incubated an additional 24 hours.

After 24 hours, the cells are harvested onto GF/C filter plates (commercially available from Packard, Downers Grove, Ill.), solubilized in Microscint 20 (Packard), and counted on a TopCount microplate scintillation and luminescence plate counter (Packard). Activity is measured as a percentage of control activity in the absence of test compound and plotted versus test compound concentration. The data are fit to a 4-parameter curve fit (Sigmaplot) and $IC_{50}$ values are calculated. As used herein, test compounds are considered non-immunosuppressive if, by using this method, the ratio of (cyclosporin A $IC_{50}$/test compound $IC_{50}$) ×100 is less than or equal to 0.02, ie., a non-immunosuppressive test compound has ≦2% of the immunosuppressive activity of cyclosporin A.

Cell viability is assessed using the MTT (3-[4,5-dimethylthiazoyl-2-yl]2,5-diphenyl-tetrazolium bromide) dye assay as described by Nelson et al., *Journal of Immunology*, Vol. 150, No. 6, pp. 2139–2147 (1993), with the exception that the assay is carried out in serum-free, phenol red-free RPMI 1640 and the dye is solubilized in 100 µL/well DMSO and read at an OD of 540 nm with a background correction at 650 nm on a SpectraMax Plus microplate reader (Molecular Devices, Menlo Park, Calif.).

Multi-Drug Resistance

As disclosed herein, the present compounds are also useful, for example, to increase the antiproliferative activity of a drug and / or prevent and / or treat multi-drug resistance. The present compounds may be assayed for this property as described in U.S. Pat. No. 5,744,485, Zelle et al., assigned to Vertex Pharmaceuticals Inc., issued Apr. 28, 1998, U.S. Pat. No. 5,726,184, Zelle et al., assigned to Vertex Pharmaceuticals Inc., issued Mar. 10, 1998, U.S. Pat. No. 5,620,971, Armistead et al., assigned to Vertex Pharmaceuticals Inc., issued Apr. 15, 1997, and U.S. Pat. No. 5,543,423, Zelle et al., assigned to Vertex Pharmaceuticals Inc., issued Aug. 6, 1996.

Methods of Making

The compounds of the present invention are prepared according to methods which are well-known to those skilled in the art. The starting materials used in preparing the compounds of the invention are known, made by known methods, or are commercially available as a starting material.

It is recognized that the skilled artisan in the art of organic chemistry can readily carry out standard manipulations of organic compounds without further direction. Examples of such manipulations are discussed in standard texts such as J. March, *Advanced Organic Chemistry*, John Wiley & Sons, 1992.

The skilled artisan will readily appreciate that certain reactions are best carried out when other functionalities are masked or protected in the compound, thus increasing the yield of the reaction and/or avoiding any undesirable side reactions. Often, the skilled artisan utilizes protecting groups to accomplish such increased yields or to avoid the undesired reactions. These reactions are found in the literature and are also well within the scope of the skilled artisan. Examples of many such manipulations can be found in, for example, T. Greene, *Protecting Groups in Organic Synthesis*, John Wiley & Sons, 1981.

The compounds of the present invention may have one or more chiral center. As a result, one may selectively prepare one optical isomer, including diastereomers and enantiomers, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as through the use of, for example, chiral salts and chiral chromatography.

In addition, it is recognized that one optical isomer, including a diastereomer and enantiomer, or a stereoisomer, may have favorable properties over the other. Thus, when disclosing and claiming the invention, when one racemic mixture is disclosed, it is clearly contemplated that both optical isomers, including diastereomers and enantiomers, or stereoisomers substantially free of the other are disclosed and claimed as well.

The following provides non-limiting examples illustrating more specifically the methods of making various compounds of the present invention.

As used herein, the following abbreviations are used:

| Reagent | Abbreviation |
| --- | --- |
| N,N-dimethylformamide | DMF |
| 1-hydroxybenzotriazole hydrate | HOBt |
| tert-butoxycarbonyl | BOC |

-continued

| Reagent | Abbreviation |
|---|---|
| (benzotriazol-1-yloxy)tripyrrolidinophosphonium hexafluorophosphate (commercially available from Fluka Chemical, Switzerland) | PyBOP |
| tetrahydrofuran | THF |
| 1-ethyl-3-(3-dimethylaminopropyl)carbodiimide | EDAC |
| phenyl (moiety) | Ph |
| trimethylsilyl trifluoromethanesulfonate | TMS-OTf |
| N,N-diisopropylethylamine | i-Pr$_2$NEt or i-Pr$_2$EtN |
| trifluoroacetic acid | TFA |
| lithium hydroxide | LiOH |

EXAMPLE 1

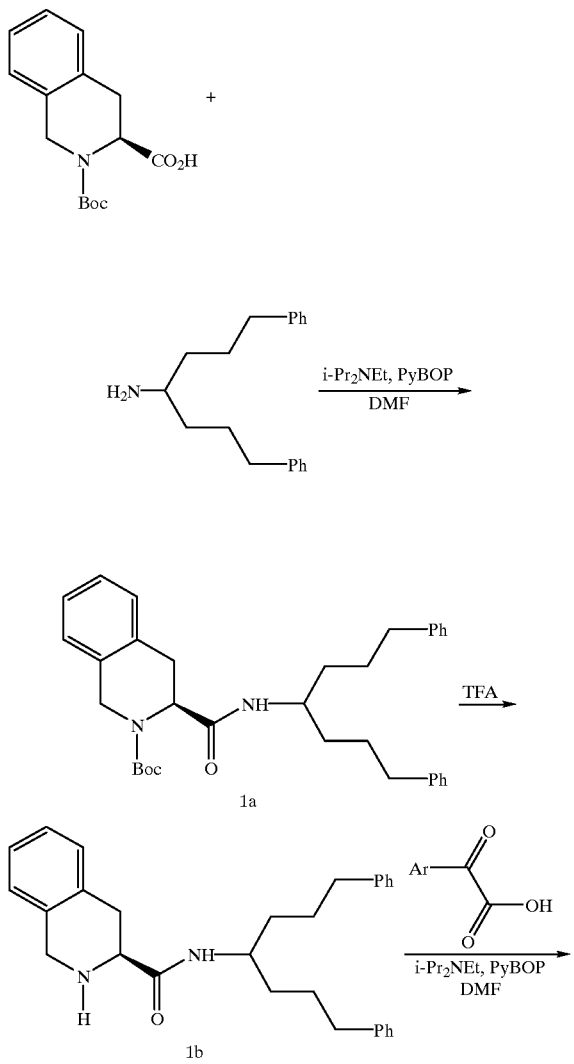

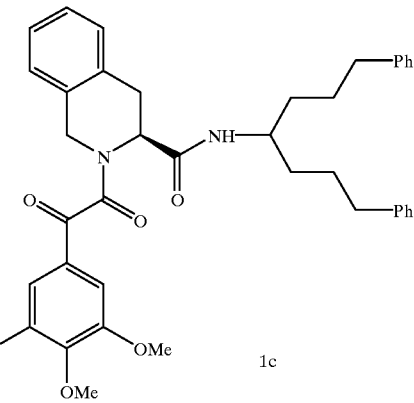

1a. (S)-(N-tert-Butoxycarbonyl)-1,2,3,4-tetrahydro-3-isoquinoline carboxylic acid 1,7-diphenyl-4-heptylamide: (S)-(N-tert-Butoxycarbonyl)-1,2,3,4-tetrahydro-3-isoquinoline carboxylic acid (4.90 g, 17.7 mmol) is dissolved in 160 mL of DMF. 1,7-Diphenyl-4-aminoheptane (4.30 g, 16.1 mmol) and i-Pr$_2$NEt (4.16 g, 32.2 mmol) are added followed by PyBOP (8.80 g, 16.9 mmol). The reaction is stirred for 18.5 hours at room temperature, then poured onto ice-cold 0.1N HCl (600 mL) and extracted with ethyl acetate (600 mL). The organic layer is washed successively with brine (100 mL), saturated NaHCO$_3$ solution (300 mL), and brine (2×200 mL). The organic solution is dried over MgSO$_4$, filtered, and concentrated under reduced pressure. Purification of the product by chromatography on silica gel affords the desired amide 1a.

1b. (S)-1,2,3,4-tetrahydro-3-isoquinoline carboxylic acid 1,7-diphenyl-4-heptylamide: The amide 1a (8.07 g, 15.3 mmol) is dissolved in 150 mL of anhydrous dichloromethane. TFA (120 mL) is added dropwise over a five minute period. After 2 hours the mixture is cooled in an ice-bath and saturated K$_2$CO$_3$ solution is added until the pH is approximately 8. The mixture is transferred to a separatory funnel containing dichloromethane (200 mL) and water (200 mL) and shaken. The organic layer is washed with water (200 mL) before drying over MgSO$_4$. The mixture is filtered and concentrated under reduced pressure to afford the desired amine 1b.

1c. (S)-N-(3', 4',5'-Trimethoxyphenylglyoxyl)-1,2,3,4-tetrahydro-3-isoquinoline carboxylic acid 1,7-diphenyl-4-heptylamide: The amine 1b (5.58 g, 13.1 mmol) is dissolved in 150 mL of anhydrous DMF. 3',4',5'-Trimethoxyphenylglyoxylic acid (3.93 g, 16.4 mmol) and i-Pr$_2$NEt (4.23 g, 32.7 mmol) are added followed by PyBOP (8.85 g, 17.0 mmol). The reaction is stirred for 18 hours at room temperature, then poured onto ice-cold 0.1N HCl (600 mL) and extracted with ethyl acetate (600 mL). The organic layer is washed successively with brine (100 mL), saturated NaHCO$_3$ solution (300 mL), and brine (2×100 mL). The organic solution is dried over MgSO$_4$, filtered, and concentrated under reduced pressure. Purification of the product by chromatography on silica gel affords the desired amide 1c.

EXAMPLE 2

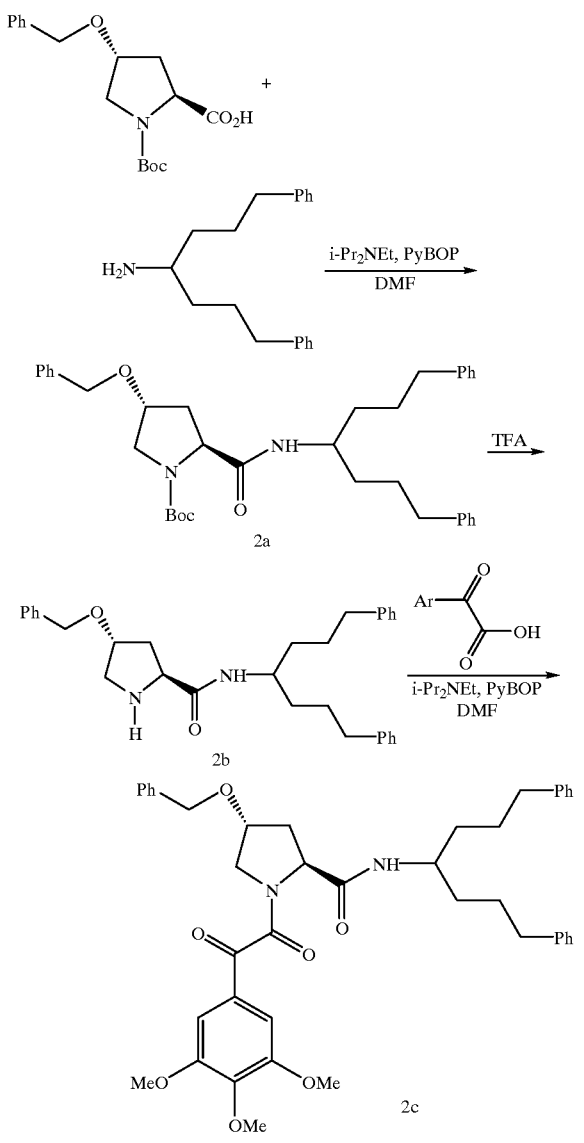

the pH is approximately 8. The mixture is transferred to a separatory funnel containing dichloromethane (300 mL) and water (300 mL) and shaken. The organic layer is washed with water (100 mL) before drying over $MgSO_4$. The mixture is filtered and concentrated in vacuo to afford the desired amine 2b.

2c. N-(3',4',5'-Trimethoxyphenylglyoxyl)-4(R)-benzyloxypyrrolidine-2(S)-carboxylic acid 1,7-diphenyl-4-heptylamide: The amine 2b (5.65 g, 12.0 mmol) is dissolved in 140 mL of anhydrous DMF. 3',4',5'-Trimethoxyphenylglyoxylic acid (3.6 g, 15.0 mmol) and i-$Pr_2$NEt (3.9 g, 30.0 mmol) are added followed by PyBOP (8.12 g., 15.6 mmol). The reaction is stirred for 18 hours at room temperature, then poured onto ice-cold 0.1N HCl (600 mL) and extracted with ethyl acetate (600 mL). The layers are separated and the organic layer is washed successively with brine (100 mL), saturated $NaHCO_3$ solution (300 mL), and brine (2×100 mL). The organic solution is dried over $MgSO_4$, filtered and concentrated in vacuo. Purification of the product on silica gel affords the desired amide 2c.

EXAMPLE 3

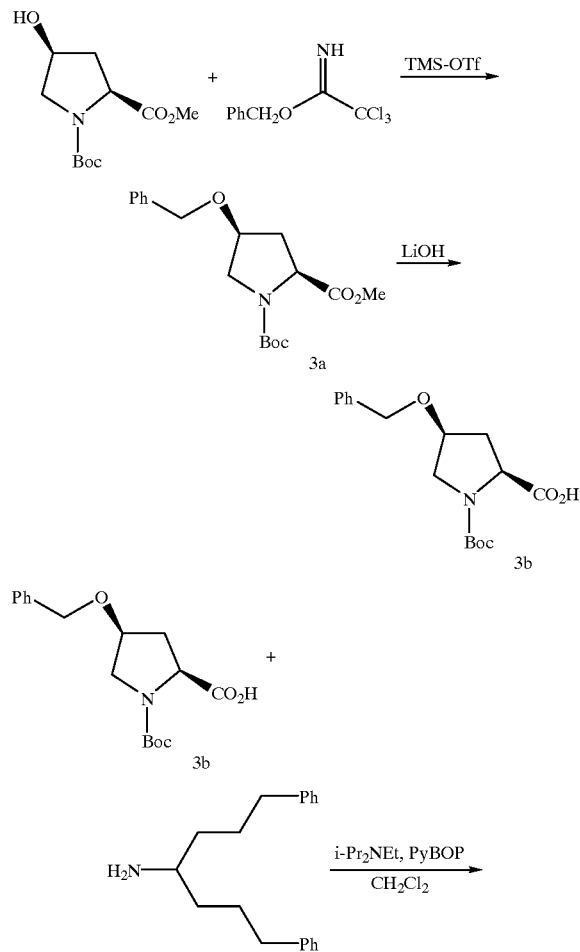

2a. (N-tert-Butoxycarbonyl)-4(R)-benzyloxypyrrolidine-2(S)-carboxylic acid 1,7-diphenyl-4-heptylamide: (N-tert-Butoxycarbonyl)-4(R)-benzyloxypyrrolidine-2(S)-carboxylic acid (5.68 g, 17.7 mmol) is dissolved in 160 mL of DMF. 1,7-Diphenyl-4-aminoheptane (4.30 g. 16.1 mmol) and i-$Pr_2$NEt (4.16 g, 32.2 mmol) are added followed by PyBOP (9.20 g, 17.1 mmol). The reaction is stirred for 20.5 hours at room temperature, then poured onto ice-cold 0.1N HCl (600 mL) and extracted with ethyl acetate (600 mL). The layers are separated and the organic layer washed successively with brine (100 mL), saturated $NaHCO_3$ solution (300 mL), and brine (2×200 mL). The organic solution is dried over $MgSO_4$, filtered, and concentrated under reduced pressure. Purification of the product on silica gel affords the desired amide 2a.

2b. 4(R)-benzyloxypyrrolidine-2(S)-carboxylic acid 1,7-diphenyl-4-heptylamide: The amide 2a (9.04 g, 16.5 mmol) is dissolved in 160 mL of anhydrous dichloromethane. TFA (130 mL) is added dropwise over a 5 minute period. After 45 minutes the mixture is cooled in an ice-bath and saturated $K_2CO_3$ solution is added until

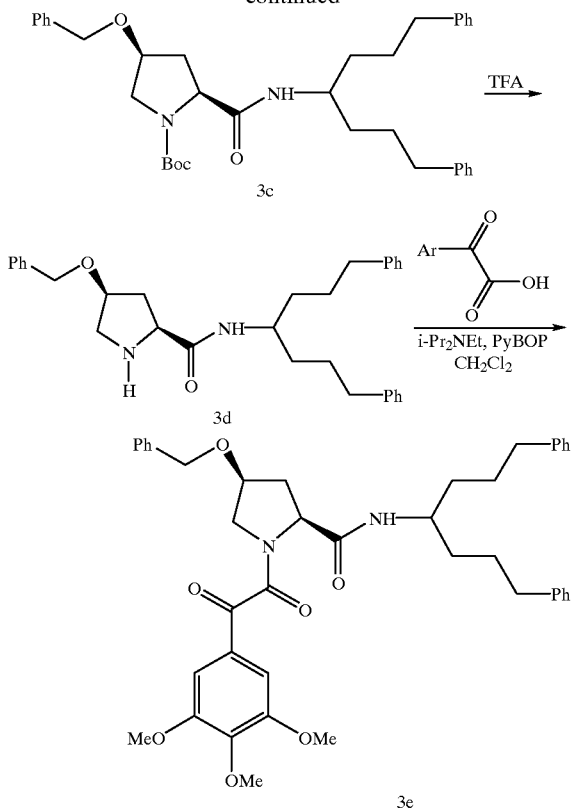

3a. Methyl (N-tert-butoxycarbonyl)-4(S)-benzyloxypyrrolidine-2(S)-carboxylate: Methyl (N-tert-butoxycarbonyl)-4-(S)-hydroxypyrrolidine-2(S)-carboxylate (6.0 g, 24.5 mmol) is dissolved in 36 mL of hexane and 18 mL of dichloromethane and benzyl trichloroacetimidate (7.72 g., 30.6 mmol) is added. The solution cooled in an ice-bath and TMS-OTf (15 drops) is added. The ice-bath is removed and the mixture is stirred at room temperature for sixteen hours. More TMS-OTf (10 drops) is added and the reaction is stirred for an additional four hours. The mixture is filtered and the solid washed with 10 mL of 2:1 hexane:dichloromethane. The combined filtrate and washings are poured onto saturated $NaHCO_3$ solution (300 mL) and extracted with ether (300 mL). The organic layer is then washed with water (200 mL), dried over $MgSO_4$, filtered, and concentrated in vacuo. The product is purified on silica gel to afford the desired ester 3a.

3b. (N-tert-butoxycarbonyl)-4(S)-benzyloxypyrrolidine-2(S)-carboxylic acid: Ester 3a (5.47 g, 16.3 mmol) is dissolved in 75 mL of a 2:2:1 mixture of THF:water:methanol. LiOH (3.91 g, 163.0 mmol) is added and the mixture is stirred at room temperature. After about 3 hours the mixture is poured onto 110 mL of saturated citric acid solution and extracted with 220 mL of ethyl acetate. The organic extract is washed with water (2×10 mL) and brine (50 mL), then dried over $MgSO_4$, filtered, and concentrated in vacuo to afford the desired carboxylic acid 3b.

3c. (N-tert-Butoxycarbonyl)-4(S)-benzyloxypyrrolidine-2(S)-carboxylic acid 1,7-diphenyl-4-heptylamide: The acid 3b (4.43 g, 13.8 mmol) is dissolved in 150 mL of dichloromethane. 1,7-Diphenyl-4-aminoheptane hydrochloride (5.24 g., 17.2 mmol) and i-$Pr_2$NEt (5.8 g, 44.8 mmol) are added followed by PyBOP (8.97 g, 17.2 mmol). The reaction is stirred for about 15 hours at room temperature, then poured onto ice-cold 0.1N HCl (100 mL) and extracted with dichloromethane (200 mL). The organic layer is washed successively with saturated $NaHCO_3$ solution (100 mL) and brine (50 mL). The organic solution is dried over $MgSO_4$, filtered, and concentrated under reduced pressure. Purification of the product on silica gel affords the desired amide 3c.

3d. 4(SR)-benzyloxypyrrolidine-2(S)-carboxylic acid 1,7-diphenyl-4-heptylamide: The amide 3c (7.07 g, 12.4 mmol) is dissolved in 120 mL of anhydrous dichloromethane. TFA (100 mL) is added dropwise over a five minute period. After 2 hours the mixture is cooled in an ice-bath and saturated $K_2CO_3$ solution is added until the pH is approximately 8. The mixture is transferred to a separatory funnel containing dichloromethane (300 mL) and water (300 mL) and shaken. The organic layer is washed with water (150 mL) before drying over $MgSO_4$. The mixture is filtered and concentrated in vacuo to afford the desired amine 3d.

3e. N-(3',4',5'-Trimethoxyphenylglyoxyl)-4(S)-benzyloxypyrrolidine-2(S)-carboxylic acid 1,7-diphenyl-4-heptylamide: The amine 3d (5.61 g, 11.9 mmol) is dissolved in 200 mL of anhydrous dichloromethane. 3',4',5'-Trimethoxyphenylglyoxylic acid (4.3 g, 18 mmol) and i-$Pr_2$NEt (3.85 g., 29.8 mmol) are added followed by PyBOP (9.3 g, 18 mmol). The reaction is stirred for about 15 hours at room temperature, then poured onto ice-cold 0.1N HCl (200 mL) and extracted with dichloromethane (300 mL). The layers are separated and the organic layer is washed successively with saturated $NaHCO_3$ solution (200 mL) and brine (100 mL). The organic solution is dried over $MgSO_4$, filtered, and concentrated in vacuo. Purification of the product on silica gel affords the desired amide 3e.

EXAMPLE 4

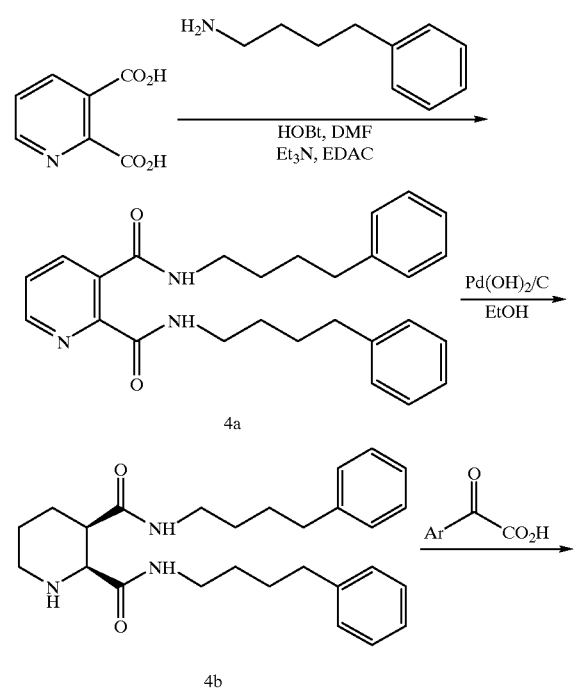

37
-continued

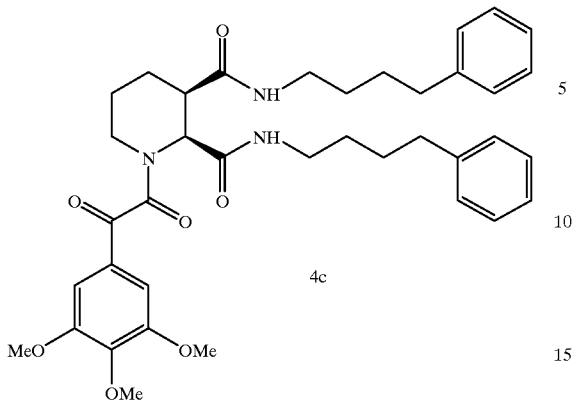

4a. 2,3-Pyridinedicarboxylic acid bis(1-phenylbutylamide): 2,3-Pyridinedicarboxylic acid (3.0 g, 18.0 mmol) is combined with HOBT (7.3 g, 54 mmol) at ambient temperature under inert atmosphere. Anhydrous DMF (150 mL) is added followed by 4-phenylbutylamine (6.24 mL, 39 mmol), triethylamine (5.0 mL, 36 mmol), and EDAC (8.6 g, 45 mmol) in succession. The reaction mixture is stirred for 18 hours at ambient temperature under inert atmosphere then poured onto ethyl acetate (500 mL) and extracted successively with water (250 mL), 1N HCl (150 mL), and brine (100 mL). The organic solution is dried over $MgSO_4$, filtered, and concentrated in vacuo to afford the desired bis-amide 4a.

4b. cis-2,3-Piperidinedicarboxylic acid bis(1-phenylbutylamide): The bis-amide 4a (5.5 g, 12.8 mmol) is dissolved in absolute ethanol (50 mL) at ambient temperature and transferred to a low pressure hydrogenation vessel containing Pearlman's catalyst (20 weight percent $Pd(OH)_2$ on carbon, 1.0 g). The mixture is hydrogenated at 50 psi until the reduction is complete. The catalyst is removed by filtration through a pad of diatomaceous earth and the filtrate is concentrated under reduced pressure. Purification of the crude product by preparative chromatography (silica gel; gradient elution with 95:5:0.1 to 80:20:0.1 methylene chloride:methanol::concentrated ammonium hydroxide) affords the desired piperidine bis-amide 4b.

4c. N-(3',4',5'-Trimethoxyphenylglyoxyl)-cis-2,3-piperidine dicarboxylic acid bis(1-phenylbutylamide): The piperidine bis-amide 4b (2.12 g, 4.87 mmol) is dissolved in anhydrous dichloromethane (30 mL) at ambient temperature under inert atmosphere. 3',4',5'-Trimethoxyphenylglyoxylic acid (1.5 g, 6.08 mmol) and EDAC (1.22 g, 6.36 mmol) are added in succession. The reaction is stirred for 18 hours at ambient temperature under inert atmosphere then poured onto water (50 mL) and extracted with ethyl acetate (50 mL). The organic layer is washed successively with 0.1N HCl (50 mL) and saturated sodium bicarbonate solution (50 mL). The organic solution is dried over $MgSO_4$, filtered and concentrated under reduced pressure. Purification of the crude product by preparative chromatography on silica gel affords the desired α-ketoamide 4c.

38
EXAMPLE 5

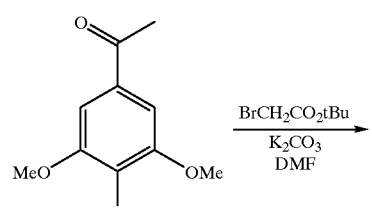

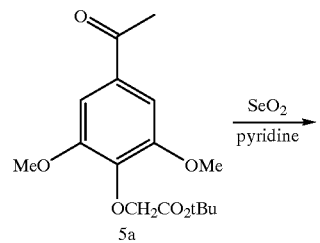

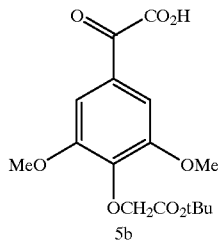

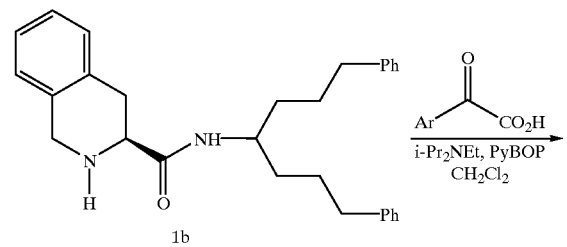

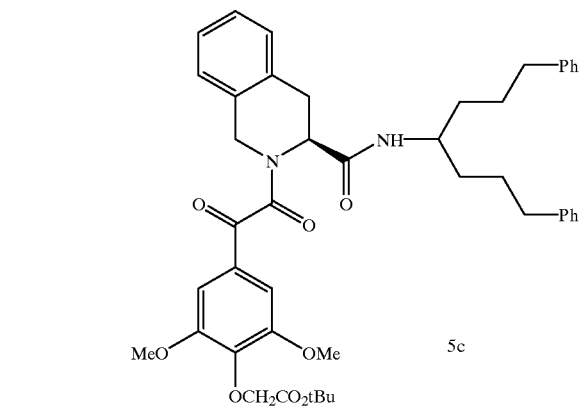

5a. 3',5'-Dimethoxy-4'-tert-butylacetoxyacetophenone: 3',5'-Dimethoxy-4'-hydroxyacetophenone (5.0 g, 25.5 mmol) is dissolved in anhydrous DMF (50 mL) at ambient temperature. Freshly ground potassium carbonate (5.3 g, 38.3 mmol) is added followed by tert-butylbromoacetate (5.65 mL, 38.3 mL). The reaction mixture is stirred for 18 hours at ambient temperature then poured onto water (500 mL) and extracted with ethyl acetate (3×100 mL). The combined organic layers are washed successively with water (50 mL), and brine (50 mL). The organic solution is dried over $MgSO_4$, filtered, and concentrated under reduced pressure. Purification of the crude product by preparative chromatography (silica gel) affords the desired acetophenone 5a.

5b. 3',5'-Dimethoxy-4'-tert-butylacetoxyphenylglyoxylic acid: The previously described 3',5'-dimethoxy-4'-tert-butylacetoxyacetophenone 5a (8.03 g, 25.9 mmol) is dissolved in anhydrous pyridine (100 mL) at ambient temperature. Selenium dioxide (5.78 g, 52.1 mmol) is added in one portion and the resulting mixture is carefully heated to reflux. After 24 hours at reflux the reaction mixture is cooled to room temperature then filtered through a pad of diatomaceous earth, washed with pyridine, and concentrated under reduced pressure. The residue is dissolved in ethyl acetate (600 mL) then extracted successively with 1N HCl (250 mL), and saturated sodium bicarbonate solution (2×200 mL). The combined bicarbonate washes are carefully acidified with concentrated HCl then poured onto 1N HCl (100 mL) and extracted with ethyl acetate (2×200 mL). The combined ethyl acetate extracts are dried over MgSO$_4$, filtered, and concentrated in vacuo to afford the desired α-ketoacid 5b.

5c. (S)-N-(3',5'-Dimethoxy-4'-tert-butylacetoxyphenylglyoxyl)-1,2,3,4-tetrahydro-3-isoquinoline carboxylic acid 1,7-diphenyl-4-heptylamide: The previously described amine 5b (5.27 g., 12.4 mmol) is dissolved in anhydrous dichloromethane (150 mL) at ambient temperature. 3',5'-Dimethoxy-4'-tert-butylacetoxyphenylglyoxylic acid (8.6 g, 25.3 mmol) is added followed by i-Pr$_2$NEt (6.44 mL, 37 mmol) and PyBOP (7.1 g, 13.6 mmol) in succession. The reaction is stirred for 18 hours at ambient temperature then poured onto ethyl acetate (800 mL) and washed successively with 0.1N HCl (200 mL), saturated sodium bicarbonate solution (2×150 mL), and brine (50 mL). The organic solution is dried over MgSO$_4$, filtered, and concentrated in vacuo. Purification of the product by preparative chromatography over silica gel affords the desired α-ketoamide 5c.

EXAMPLE 6

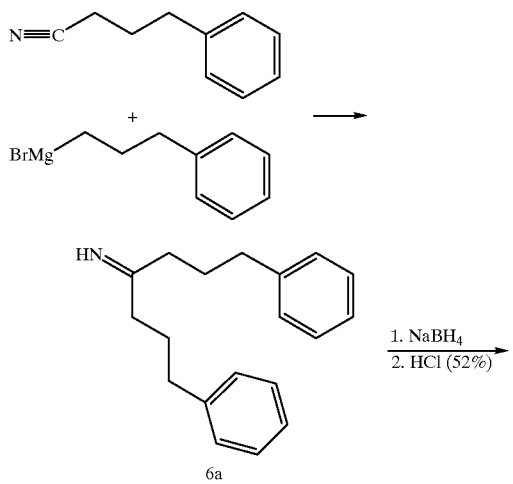

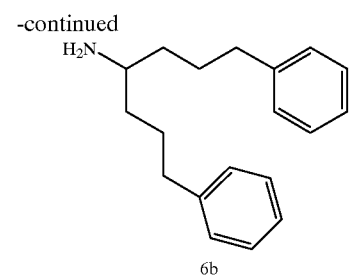

6a. Magnesium (40.2 g, 1.65 mol) and anhydrous ether (3.2 L) are combined in a reaction vessel with stirring. A solution of 1-bromo-3-phenyl propane in 1.6 L of anhydrous ether is added to an addition funnel. The bromide solution is added dropwise to the stirring reaction vessel over a 1 hour period. Upon completion of addition, the mixture stirs for 1–2 hours. A solution of 4-phenylbutyronitrile (160 g, 1.1 mol) in anhydrous ether (2.4 L) is placed in the addition funnel. The solution is added to the reaction vessel over a 1 hour time period. Upon complete addition the solution is heated to reflux for 10 hours, and then stirs at room temperature for six hours.

6b. 1,7-Diphenyl-4-aminoheptane: The reaction mixture of 6a is diluted with methanol (3.2 L) using an addition funnel. Sodium borohydride (83.4 g, 2.2 mol) is added in portions. Upon complete addition the reaction is stirred at room temperature for six hours. The reaction mixture is quenched by a slow addition of water (3.2 L). The mixture is diluted with ether (3.2 L) and water (1.6 L). The ether layer is separated and the aqueous layer is extracted twice with ether (3.2 L×2). The combined ether extracts are washed once with sodium chloride solution, dried, filtered, and concentrated in vacuo to give the crude product. This product is diluted in ether (1.2 L) and acidified by slow addition of 1M HCl (1.2 L). The mixture stirs for one hour and is concentrated in vacuo. The resulting precipitate is diluted with acetonitrile and is stirred for 16 hours. The desired 1,7-Diphenyl-4-aminoheptane is collected by filtration.

Use of the Present Compounds

The compounds herein may be used for the treatment of such conditions as, for example, treating hair loss in mammals, including arresting and/or reversing hair loss and promoting hair growth. Such conditions may manifest themselves in, for example, alopecia, including male pattern baldness and female pattern baldness.

While certain of the present compounds may exhibit immunosuppressive activity, the preferred compounds of the present invention are, as defined herein, non-immunosuppressive.

Furthermore, in addition to treating hair loss, the compounds of the present invention may be used to treat a variety of clinical conditions which include, but are not limited to, multi-drug resistance (particularly for use in cancer chemotherapy), neurological disorders and neurodegenerative diseases, cardiac injury associated with ischemia/reperfusion injury, and treatment of fungal, microbial, viral (especially HIV), malarial or other parasitic diseases or conditions. The present compounds may also be useful as inhibitors of multi-drug transporter proteins to enhance, for example, pharmacokinetics and bioavailability. Certain compounds of the present invention may exhibit immunomodulatory properties. These compounds would prove useful in the treatment of organ transplant rejection and various autoimmune diseases which include, but are not limited to, Behcet's disease, Crohn's disease, systemic lupus erythematosus, psoriasis, rheumatoid arthritis, eczema, multiple sclerosis, myasthenia gravis, insulin-dependent diabetes mellitus, and Graves' disease. In addition, the present compounds may have utility for the treatment of certain inflammatory and allergic disease states, including urticaria, allergic contact dermatitis, atopic dermatitis, atopic keratoconjunctivitis, inflammatory bowel disease, and asthma. The present compounds may also be useful in the treatment of cardiac hypertrophy in congestive heart failure.

The present compounds may also be useful in combination with a matrix metalloproteinase inhibitor for treatment of various conditions including, for example, tissue destructive diseases mediated by excessive metalloproteinase activity, cancer, and multi-drug resistance, as well as all of the conditions previously mentioned herein above. Particularly preferred matrix metalloproteinase inhibitors useful in such combination include those described in U.S. patent application Ser. No. 60/024,765, Pikul et al., assigned to The Procter & Gamble Co., filed Aug. 28, 1996, U.S. patent application Ser. No. 60/024,842, Natchus et al., assigned to The Procter & Gamble Co., filed Aug. 28, 1996, U.S. patent application Ser. No. 60/024,846, Pikul et al., assigned to The Procter & Gamble Co., filed Aug. 28, 1996, U.S. patent application Ser. No. 60/024,746, Almstead et al., assigned to The Procter & Gamble Co., filed Aug. 28, 1996, U.S. patent application Ser. No. 60/024,830, Pikul et al., assigned to The Procter & Gamble Co., filed Aug. 28, 1996, U.S. patent application Ser. No. 60/024,764, De et al., assigned to The Procter & Gamble Co., filed Aug. 28, 1996, U.S. patent application Ser. No. 60/024,764, De et al., assigned to The Procter & Gamble Co., filed Aug. 28, 1996, and U.S. patent application Ser. No. 60/024,766, Wang et al., assigned to The Procter & Gamble Co., filed Aug. 28, 1996.

Preferably, the compounds of the present invention are formulated into pharmaceutical compositions for use in treatment or prophylaxis of conditions such as the foregoing. Standard pharmaceutical formulation techniques are used, such as those disclosed in *Remington's Pharmaceutical Sciences,* Mack Publishing Company, Easton, Pa. (1990).

Typically, from about 5 mg to about 3000 mg, more preferably from about 5 mg to about 1000 mg, more preferably from about 10 mg to about 100 mg, of a compound of the present invention is administered per day for systemic administration. It is understood that these dosage ranges are by way of example only, and that daily administration can be adjusted depending on various factors. The specific dosage of the compound to be administered, as well as the duration of treatment, and whether the treatment is topical or systemic are interdependent. The dosage and treatment regimen will also depend upon such factors as the specific compound used, the treatment indication, the efficacy of the compound, the personal attributes of the subject (such as, for example, weight, age, sex, and medical condition of the subject), compliance with the treatment regimen, and the presence and severity of any side effects of the treatment.

In addition to the subject compound, the compositions of the subject invention contain a pharmaceutically-acceptable carrier ("carrier"). The term pharmaceutically-acceptable carrier, as used herein, means one or more compatible solid or liquid filler diluents or encapsulating substances which are suitable for administration to a mammal. The term "compatible", as used herein, means that the components of the composition are capable of being commingled with a compound of the present invention, and with each other, in a manner such that there is no interaction which would substantially reduce the efficacy of the composition under ordinary use situations. Carriers must, of course, be of sufficiently high purity and sufficiently low toxicity to render them suitable for administration to the animal, preferably mammal, being treated. The carrier can itself be inert or it can possess pharmaceutical benefits of its own.

The compositions of this invention may be in any of a variety of forms, suitable (for example) for oral, rectal, topical, nasal, ocular or parenteral administration. Of these, topical or oral administration is especially preferred. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the activity of the compound of the present invention. The amount of carrier employed in conjunction with the compound is sufficient to provide a practical quantity of material for administration per unit dose of the compound. Techniques and compositions for making dosage forms useful in the methods of this invention are described in the following references: *Modern Pharmaceutics,* Chapters 9 and 10, Banker & Rhodes, eds. (1979); Lieberman et al., *Pharmaceutical Dosage Forms: Tablets* (1981); and Ansel, *Introduction to Pharmaceutical Dosage Forms,* $2^{nd}$ Ed., (1976).

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

Various oral dosage forms can be used, including such solid forms as tablets, capsules, granules and bulk powders. These oral forms comprise a safe and effective amount, usually at least about 5%, and preferably from about 25% to about 50%, of a compound of the present invention. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for oral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components depends on secondary considerations like taste, cost, and shelf stability, which are not critical for the purposes of the subject invention, and can be readily made by a person skilled in the art.

Orally administered compositions also include liquid solutions, emulsions, suspensions, powders, granules, elixirs, tinctures, syrups, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compounds of the present invention may also be topically administered. The carrier of the topical composition preferably aids penetration of the present compounds into the skin to reach the environment of the hair follicle. Topical compositions of the present invention may be in any form including, for example, solutions, creams, ointments, gels, lotions, shampoos, leave-on and rinse-out hair conditioners, milks, cleansers, moisturizers, sprays, skin patches, and the like.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polythylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines. A preferred formulation for topical delivery of the present compounds utilizes liposomes such as described in Dowton et al., "Influence of Liposomal Composition on Topical Delivery of Encapsulated Cyclosporin A: I. An in vitro Study Using Hairless Mouse Skin", *S.T.P. Pharma Sciences,* Vol. 3, pp. 404–407 (1993), Wallach and Philippot, "New Type of Lipid Vesicle: Novasome®", *Liposome Technology,* Vol. 1, pp. 141–156 (1993), and Wallach, U.S. Pat. No. 4,911,928, assigned to Micro-Pak, Inc., issued Mar. 27, 1990.

The compounds of the present invention may also be administered by iontophoresis. See, e.g., www.unipr.it/arpa/dipfarm/erasmus/erasm14.html, Banga et al., "Hydrogel-based Iontotherapeutic Delivery Devices for Transdermal Delivery of Peptide/Protein Drugs", *Pharm. Res.,* Vol. 10 (5), pp. 697–702 (1993), Ferry L. L., "Theoretical Model of Iontophoresis Utilized in Transdermal Drug Delivery",

*Pharmaceutical Acta Helvetiae*, Vol 70, pp. 279–287 (1995), Gangarosa et al., "Modem Iontophoresis for Local Drug Delivery", *Int. J. Pharm*, Vol. 123, pp. 159–171 (1995), Green et al., "Iontophoretic Delivery of a Series of Tripeptides Across the Skin in vitro", *Pharm. Res.*, Vol 8, pp. 1121–1127 (1991), Jadoul et al., "Quantification and Localization of Fentanyl and TRH Delivered by Iontophoresis in the Skin", *Int. J. Pharm.*, Vol. 120, pp. 221–8 (1995), O'Brien et al., "An Updated Review of its Antiviral Activity, Pharmacokinetic Properties and Therapeutic Efficacy", *Drugs*, Vol. 37, pp. 233–309 (1989), Parry et al., "Acyclovir Biovailability in Human Skin", *J. Invest. Dermatol.*, Vol. 98 (6), pp. 856–63 (1992), Santi et al., "Drug Reservoir Composition and Transport of Salmon Calcitonin in Transdermal Iontophoresis", *Pharm. Res.*, Vol 14 (1), pp. 63–66 (1997), Santi et al., "Reverse Iontophoresis—Parameters Determining Electroosmotic Flow: I. pH and Ionic Strength", *J. Control. Release*, Vol. 38, pp. 159–165 (1996), Santi et al., "Reverse Iontophoresis—Parameters Determining Electroosmotic Flow: II. Electrode Chamber Formulation", *J. Control. Release*, Vol. 42, pp. 29–36 (1996), Rao et al., "Reverse Iontophoresis: Noninvasive Glucose Monitoring in vivo in Humans", *Pharm. Res.*, Vol. 12 (12), pp. 1869–1873 (1995), Thysman et al., "Human Calcitonin Delivery in Rats by Iontophoresis", *J. Pharm. Pharmacol.*, Vol. 46, pp. 725–730 (1994), Volpato et al., "Iontophoresis Enhances the Transport of Acyclovir through Nude Mouse Skin by Electrorepulsion and Electroosmosis", *Pharm. Res.*, Vol. 12 (11), pp. 1623–1627 (1995).

The compositions of the present invention may also optionally comprise an activity enhancer. The activity enhancer can be chosen from a wide variety of molecules which can function in different ways to enhance hair growth effects of a compound of the present invention. Particular classes of activity enhancers include other hair growth stimulants and penetration enhancers.

Additional hair growth stimulants can be chosen from a wide variety of molecules which can function in different ways to enhance the hair growth effects of a compound of the present invention. These optional other hair growth stimulants, when present, are typically employed in the compositions herein at a level ranging from about 0.01% to about 15%, preferably from about 0.1% to about 10%, most preferably from about 0.5% to about 5% by weight of the composition.

Vasodilators such as potassium channel agonists including, for example, minoxidil and minoxidil derivatives such as aminexil and such as those described in U.S. Pat. Nos. 3,382,247, 5,756,092, issued May 26, 1998, U.S. Pat. No. 5,772,990, issued Jun. 30, 1998, U.S. Pat. No. 5,760,043, issued Jun. 2, 1998, U.S. Pat. No. 328,914, issued Jul. 12, 1994, U.S. Pat. No. 5,466,694, issued Nov. 14, 1995, U.S. Pat. No. 5,438,058, issued Aug. 1, 1995, and U.S. Pat. No. 4,973,474, issued Nov. 27, 1990, (all of which are herein incorporated by reference), and cromakalin and diazoxide can be used as an additional hair growth stimulant in the compositions herein.

One suitable class of additional hair growth stimulant for use herein are antiandrogens. Examples of suitable antiandrogens may include, but are not limited 5-α-reductase inhibitors such as finasteride and those described in U.S. Pat. No. 5,516,779, issued May 14, 1996 (herein incorporated by reference) and in Nane et al., *Cancer Research* 58, "Effects of Some Novel Inhibitors of C17,20-Lyase and 5α-Reductase in vitro and in vivo and Their Potential Role in the Treatment of Prostate Cancer," as well as cyproterone acetate, azelaic acid and its derivatives and those compounds described in U.S. Pat. No. 5,480,913, issued Jan. 2, 1996, flutamide, and those described in U.S. Pat. No. 5,411,981, issued May 2, 1995, U.S. Pat. No. 5,565,467, issued Oct. 15, 1996 and U.S. Pat. No. 4,910,226, issued Mar. 20, 1990, all of which are herein incorporated by reference.

Another suitable class of optional hair growth stimulants are immunosuppressants or non-immunosuppressants such as 1) cyclosporin and cyclosporin analogs including those described in U.S. Provisional Patent Application No. 60/122,925, Fulmer et al., filed Mar. 5, 1999, herein incorporated by reference, and 2) FK506 analogs such as those described in U.S. Provisional Patent Application No. 60/147,279, Degenhardt et al., filed Aug. 5, 1999; U.S. Provisional Patent Application No. 60/147,313, Degenhardt et al., filed Aug. 5, 1999; U.S. Provisional Patent Application No. 60/147,280, Degenhardt et al., filed Aug. 5, 1999; U.S. Provisional Patent Application No. 60/147,278, Degenhardt et al., filed Aug. 5, 1999; and U.S. Provisional Patent Application No. 60/147,276, Eickhoff et al., filed Aug. 5, 1999; all of which are herein incorporated by reference.

Another suitable class of optional hair growth stimulants are antimicrobials such as selenium sulfide, ketoconazole, triclocarbon, triclosan, zinc pyrithione, itraconazole, asiatic acid, hinokitiol, mipirocin and those described in EPA 0,680,745 (herein incorporated by reference), clinacycin hydrochloride, benzoyl peroxide, benzyl peroxide and minocyclin.

Anti-inflammatories can also be incorporated into the compositions herein as an optional hair growth stimulant. Examples of suitable anti-inflammatories may include glucocorticoids such as hydrocortisone, mometasone furoate and prednisolone, nonsteroidal anti-inflammatories including cyclooxygenase or lipoxygenase inhibitors such as those described in U.S. Pat. No. 5,756,092, and benzydamine, salicylic acid, and those compounds described in EPA 0,770,399, published May 2, 1997, WO 94/06434, published Mar. 31, 1994, and FR 2,268,523, published Nov. 21, 1975, all of which are herein incorporated by reference.

Another suitable class of optional hair growth stimulants are thyroid hormones and derivatives and analogs thereof. Examples of suitable thyroid hormones for use herein may include triiodothyrionine. Examples of thyroid hormone analogs which may be suitable for use herein include those described in U.S. Provisional Patent Application No. 60/136,996, Zhang et al., filed Jun. 1, 1999, U.S. Provisional Patent Application No. 60/137,024, Zhang et al., filed Jun. 1, 1999, U.S. Provisional Patent Application No. 60/137,022, Zhang et al., filed Jun. 1, 1999, U.S. Provisional Patent Application No. 60/137,023, Zhang et al., filed Jun. 1, 1999, U.S. Provisional Patent Application No. 60/137,052, Youngquist et al., filed Jun. 1, 1999, U.S. Provisional Patent Application No. 60/137,063, Youngquist et al., filed Jun. 1, 1999, and U.S. Provisional Patent Application No. 60/136,958, Youngquist et al., filed Jun. 1, 1999.

Prostaglandin agonists or antagonists can also be used as optional hair growth stimulants in the compositions herein. Examples of suitable prostaglandins agonists or antagonists include latanoprost and those described in WO 98/33497, Johnstone, published Aug. 6, 1998, WO 95/11003, Stjernschantz, published Apr. 27, 1995, JP 97-100091, Ueno and JP 96-134242, Nakamura.

Another class of optional hair growth stimulants for use herein are retinoids. Suitable retinoids may include isotretinoin, acitretin, and tazarotene.

Another class of optional hair growth stimulants for use herein are triterpenes such as, for example, those disclosed in Bradbury et al., U.S. Pat. application Ser. No. 09/353,408, "Method for Regulating Hair Growth", filed Jul. 15, 1999 and Bradbury et al., U.S. Pat. application Ser. No. 09/353, 409, "Compositions Which Contain Triterpenes for Regulating Hair Growth", filed Jul. 15, 1999, each incorporated by reference in their entirety.

Other classes of optional hair growth stimulants for use herein include flavinoids, ascomycin derivatives and analogs, histamine antagonists such as diphenhydramine hydrochloride, other triterpenes such as oleanolic acid and ursolic acid and those described in U.S. Pat. No. 5,529,769, JP 10017431, WO 95/35103, U.S. Pat. No. 5,468,888, JP 09067253, WO 92/09262, JP 62093215, U.S. Pat. Nos. 5,631,282, 5,679,705, JP 08193094, saponins such as those described in EP 0,558,509 to Bonte et al., published Sep. 8, 1993 and WO 97/01346 to Bonte et al, published Jan. 16, 1997 (both of which are herein incorporated by reference in their entirety), proteoglycanase or glycosaminoglycanase inhibitors such as those described in U.S. Pat. No. 5,015, 470, issued May 14, 1991, U.S. Pat. No. 5,300,284, issued Apr. 5, 1994 and U.S. Pat. No. 5,185,325, issued Feb. 9, 1993 (all of which are herein incorporated in their entirety by reference) estrogen agonists and antagonists, pseudoterins, cytokine and growth factor promotors, analogs or inhibitors such as interleukinl inhibitors, interleukin-6 inhibitors, interleukin-10 promotors, and tumor necrosis factor inhibitors, vitamins such as vitamin D analogs and parathyroid hormone antagonists, Vitamin B12 analogs and panthenol, interfuron agonists and antagonists, hydroxyacids such as those described in U.S. Pat. No. 5,550,158, benzophenones, and hydantoin anticonvulsants such as phenytoin.

Other additional hair growth stimulants are described in detail in, for example, JP 09-157,139 to Tsuji et al., published Jun. 17, 1997; EP 0277455 A1 to Mirabeau, published Aug. 10, 1988; WO 97/05887 to Cabo Soler et al., published Feb. 20, 1997; WO 92/16186 to Bonte et al., published Mar. 13, 1992; JP 62-93215 to Okazaki et al., published Apr. 28, 1987; U.S. Pat. No. 4,987,150 to Kurono et al., issued Jan. 22, 1991; JP 290811 to Ohba et al., published Oct. 15, 1992; JP 05-286,835 to Tanaka et al., published Nov. 2, 1993, FR 2,723,313 to Greff, published Aug. 2, 1994, U.S. Pat. No. 5,015,470 to Gibson, issued May 14, 1991, U.S. Pat. No. 5,559,092, issued Sep. 24, 1996, U.S. Pat. No. 5,536,751, issued Jul. 16, 1996, U.S. Pat. No. 5,714,515, issued Feb. 3, 1998, EPA 0,319,991, published Jun. 14, 1989, EPA 0,357, 630, published Oct. 6, 1988, EPA 0,573,253, published Dec. 8, 1993, JP 61-260010, published Nov. 18, 1986, U.S. Pat. No. 5,772,990, issued Jun. 30, 1998, U.S. Pat. No. 5,053, 410, issued Oct. 1, 1991, and U.S. Pat. No. 4,761,401, issued Aug. 2, 1988, all of which are herein incorporated by reference.

Non-limiting examples of penetration enhancers which may be used in the compositions herein include, for example, 2-methyl propan-2-ol, propan-2-ol, ethyl-2-hydroxypropanoate, hexan-2,5-diol, POE(2) ethyl ether, di(2-hydroxypropyl) ether, pentan-2,4-diol, acetone, POE(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, POE ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, iso-propyl palmitate, ethyl laurate, 2-ethyl-hexyl pelargonate, iso-propyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hyroxyoctanoic acid, dimethyl sulphoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, and, 1-dodecylazacycloheptan-2-one.

In all of the foregoing, of course, the compounds of the invention can be administered alone or as mixtures, and the compositions may further include additional drugs or excipients as appropriate for the indication.

Composition Examples

The following composition and method examples do not limit the invention, but provide guidance to the skilled artisan to prepare and use the compounds, compositions, and methods of the invention. In each example, a compound of the present invention other than the one mentioned may be substituted in the example with similar results.

Example A

A tablet for oral administration according to the present invention is made, comprising:

| Component | Amount |
| --- | --- |
| Compound of Example 5 | 15 mg |
| Lactose | 120 mg |
| Maize Starch | 70 mg |
| Talc | 4 mg |
| Magnesium Stearate | 1 mg |

A human female subject weighing 60 kg (132 lbs), suffering from rheumatoid arthritis, is treated by a method of this invention. Specifically, for two years, a regimen of three tablets per day of the above composition is administered orally to the subject.

Example B

A composition for topical administration according to the present invention is made, comprising:

| Component | Amount |
| --- | --- |
| Compound of Example 1 | 5% |
| Ethanol | 57% |
| Propylene Glycol | 19% |
| Dimethyl Isosorbide | 19% |

A human male subject suffering from male pattern baldness is treated by a method of this invention. Specifically, for 6 weeks, the above composition is daily administered topically to the subject.

Example C

A composition for topical administration according to the present invention is made according to the method of Dowton et al., "Influence of Liposomal Composition on Topical Delivery of Encapsulated Cyclosporin A: I. An in vitro Study Using Hairless Mouse Skin", *S.T.P. Pharma Sciences*, Vol. 3, pp. 404–407 (1993), using the compound of Example 2 in lieu of cyclosporin A and using the Novasome 1 for the non-ionic liposomal formulation.

A human male subject suffering from male pattern baldness is treated each day with the above composition. Specifically, for 6 weeks, the above composition is administered topically to the subject.

Example D

A shampoo according to the present invention is made, comprising:

| Component | Ex. C-1 | Ex. C-2 | Ex. C-3 | Ex. C-4 |
|---|---|---|---|---|
| Ammonium Lauryl Sulfate | 11.5% | 11.5% | 9.5% | 7.5% |
| Ammonium Laureth Sulfate | 4% | 3% | 2% | 2% |
| Cocamide MEA | 2% | 2% | 2% | 2% |
| Ethylene Glycol Distearate | 2% | 2% | 2% | 2% |
| Cetyl Alcohol | 2% | 2% | 2% | 2% |
| Stearyl Alcohol | 1.2% | 1.2% | 1.2% | 1.2% |
| Glycerin | 1% | 1% | 1% | — |
| Polyquaternium 10 | 0.5% | 0.25% | — | — |
| Polyquaternium 24 | — | — | 0.5% | 0.25% |
| Sodium Chloride | 0.1% | 0.1% | 0.1% | 0.1% |
| Sucrose Polyesters of Cottonate Fatty Acid | 3% | 3% | — | — |
| Sucrose Polyesters of Behenate Fatty Acid | 2% | 3% | — | — |
| Polydimethyl Siloxane | — | — | 3% | 2% |
| Cocaminopropyl Betaine | — | 1% | 3% | 3% |
| Lauryl Dimethyl Amine Oxide | 1.5% | 1.5% | 1.5% | 1.5% |
| Decyl Polyglucose | — | — | 1% | 1% |
| DMDM Hydantoin | 0.15% | 0.15% | 0.15% | 0.15% |
| Compound of Example 1 | 2% | — | — | — |
| Compound of Example 4 | — | 5% | — | — |
| Compound of Example 5 | — | — | 3% | — |
| Phenoxyethanol | 0.5% | 0.5% | 0.5% | 0.5% |
| Fragrance | 0.5% | 0.5% | 0.5% | 0.5% |
| Water | q.s. | q.s. | q.s. | q.s. |

What is claimed is:

1. A compound having a structure:

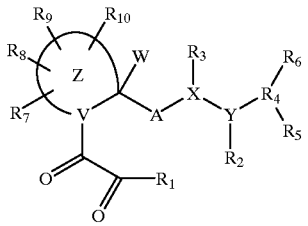

and pharmaceutically acceptable salts, hydrates, and biohydrolyzable amides, esters, and imides thereof, wherein:

(a) V is a heteroatom wherein the heteroatom is nitrogen;

(b) $R_1$ is selected from the group consisting of alkyl having at least 3 carbon atoms, alkenyl, heteroalkyl, heteroalkenyl, cycloalkyl, heterocycloalkyl, aryl, arylalkyl, heteroarylalkyl, arylalkenyl, and heteroarylalkenyl;

(c) Z is a saturated or unsaturated 6-, membered heterocycle that does not contain any heteroatoms other than the V nitrogen;

(d) K is selected from the group consisting of hydrogen, alkyl, alkenyl, heteroalkyl, heteroalkenyl, cycloalkyl, heterocycloalkyl, aryl, arylalkyl, heteroarylalkyl, arylalkenyl, and heteroarylalkenyl;

(e) W is selected from the group consisting of nil, hydrogen, and lower alkyl;

(f) A is selected from the group consisting of nil and alkyl;

(g) X and Y are each, independently, selected from the group consisting of C(O), P(O), N, O, and S, wherein:
 (i) when X is C(O) then $R_3$ is nil and Y is selected from the group consisting of N, and S;
 (ii) when X is P(O) then $R_3$ is nil and Y is selected from the group consisting of N and O;
 (iii) when X is N then $R_3$ is selected from hydrogen, alkyl, and arylalkyl, Y is selected from the group consisting of C(O) and P(O), and $R_2$ is nil;
 (iv) when X is O then $R_3$ is nil, Y is selected from the group consisting of C(O) and P(O), and $R_2$ is nil; and
 (v) when X is S then $R_3$ is nil, Y is C(O), and $R_2$ is nil;

(h) $R_2$ and $R_3$ are each, independently, selected from the group consisting of nil, hydrogen, alkyl, and arylalkyl;

(i) $R_4$ is selected from the group consisting of methylene and methyne;

(j) $R_5$ and $R_6$ are each, independently, selected from the group consisting of nil, hydrogen, alkyl having at least three carbon atoms, alkenyl, heteroalkyl, heteroalkenyl, cycloalkyl, heterocycloalkyl, aryl, arylalkyl, heteroarylalkyl, arylalkenyl, and heteroarylalkenyl; wherein at least one of $R_5$ or $R_6$ is not nil or hydrogen;

(k) $R_7$, $R_8$, and $R_9$, and $R_{10}$ are each, independently, selected from the group consisting of nil, hydrogen, alkyl, alkenyl, heteroalkyl, heteroalkenyl, cycloalkyl, heterocycloalkyl, aryl, arylalkyl, heteroarylalkyl, arylalkenyl, heteroarylalkenyl, halo, cyano, hydroxy, oxo, imino, —$R_{14}SR_{15}$, —$R_{14}S(O_2)R_{15}$, —$R_{14}S(O)R_{15}$, —$R_{14}C(O)R_{15}$, —$R_{14}C(O)NR_{15}R_{16}$, —$R_{14}C(O)OR_{15}$, —$R_{14}OR_{15}$, —$R_{14}NR_{15}R_{16}$, —$R_{14}P(O)NR_{15}R_{16}$, —$R_{14}P(O)OR_{15}R_{16}$, and a spiro moiety, and wherein $R_7$ and $R_8$ may be optionally bonded together to form an aromatic or saturated, carbocyclic or heterocyclic ring wherein the ring is fused to Z; wherein when A is nil and X is C(O) at least one of $R_7$, $R_8$, $R_9$, and $R_{10}$ is not nil or hydrogen;

(l) $R_{14}$ is selected from the group consisting of nil, alkyl, alkenyl, heteroalkyl, heteroalkenyl, cycloalkyl, heterocycloalkyl, aryl, arylalkyl, heteroarylalkyl, arylalkenyl, and heteroarylalkenyl; and (m) $R_{15}$ is selected from the group consisting of hydrogen, alkyl, alkenyl, heteroalkyl, heteroalkenyl, cycloalkyl, heterocycloalkyl, aryl, arylalkyl, heteroarylalkyl, arylalkenyl, and heteroarylalkenyl; and (n) $R_{16}$ is selected from the group consisting of hydrogen and alkyl.

2. A compound according to claim 1, wherein A is nil, X is C(O), Y is N, and $R_2$ is hydrogen.

3. A compound according to claim 2 wherein $R_8$, $R_9$, and $R_{10}$ are each, independently, selected from the group consisting of hydrogen and nil.

4. A compound according to claim 3 which is:

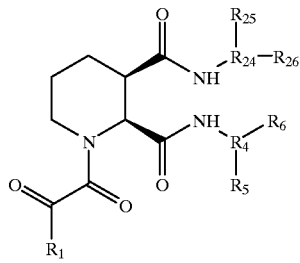

wherein $R_{24}$ is selected from the group consisting of nil, hydrogen, and alkyl, and $R_{25}$ and $R_{26}$ are each, independently, selected from the group consisting of nil, hydrogen, alkyl, alkenyl, heteroalkyl, heteroalkenyl, cycloalkyl, heterocycloalkyl, aryl, heteroaryl, arylalkyl, heteroarylalkyl, arylalkenyl, heteroarylalkenyl, halogen, hydroxy, oxo, alkoxy, aryloxy, —$SR_{27}$, —$SO_2R_{27}$, —$SOR_{27}$, —$COR_{27}$, —C(O)$OR_{27}$, —C(O)$NR_{29}R_{27}$, —$CSR_{27}$, —$OR_{27}$, and —$NR_{27}R_{28}$, wherein $R_{27}$, $R_{28}$, and $R_{29}$ are each, independently, selected from the group consisting of hydrogen, alkyl, alkenyl, heteroalkyl, heteroalkenyl, cycloalkyl, heterocycloalkyl, aryl, heteroaryl, arylalkyl, heteroarylalkyl, arylalkenyl, and heteroarylalkenyl.

5. A compound according to claim 4 which is selected from the group consisting of:

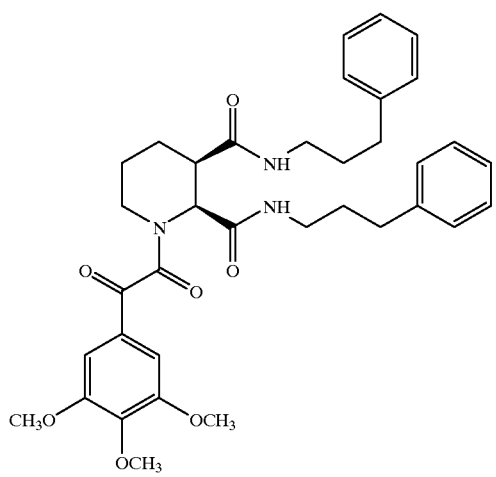

and

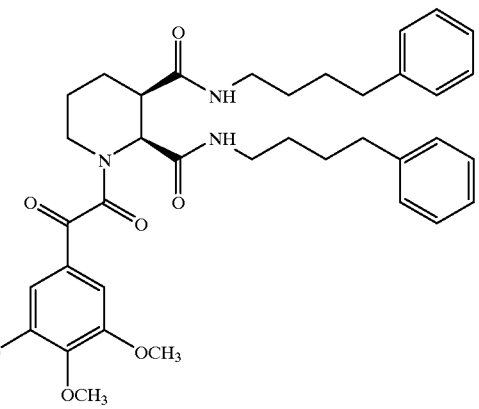

6. A compound according to claim 2 wherein $R_7$ and $R_8$ are bonded together to form a carbocyclic or heterocyclic aromatic ring.

7. A compound according to claim 6 which is selected from the group consisting of:

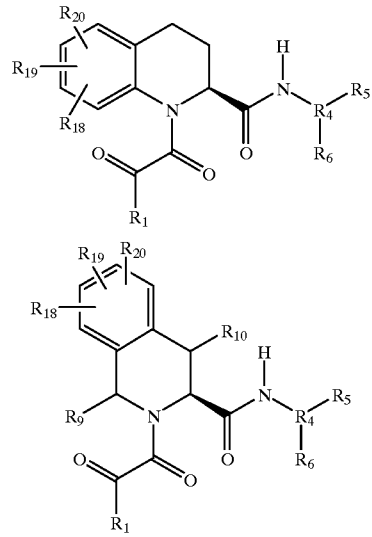

and

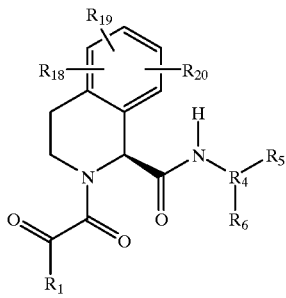

wherein $R_{18}$, $R_{19}$, and $R_{20}$ are each, independently, selected from the group consisting of nil, alkyl, alkenyl, heteroalkyl, heteroalkenyl, cycloalkyl, heterocycloalkyl, aryl, heteroaryl, arylalkyl, heteroarylalkyl, arylalkenyl, heteroarylalkenyl, halogen, hydroxy, oxo, alkoxy, aryloxy, —$SR_{21}$, —$S(O_2)R_{21}$, —$S(O)R_{21}$, —$C(O)R_{21}$, —$C(O)OR_{21}$, —$C(O)NR_{21}R_{23}$, —$C(S)R_{21}$, —$OR_{21}$, and —$NR_{21}R_{22}$, and wherein $R_{18}$ and $R_{19}$ may be bonded together to form a 5-, 6-, or 7-membered carbocyclic or heterocyclic ring; wherein $R_{21}$, $R_{22}$, and $R_{23}$ are each, independently, selected from the group consisting of hydrogen, alkyl, alkenyl, heteroalkyl, heteroalkenyl, cycloalkyl, heterocycloalkyl, aryl, heteroaryl, arylalkyl, heteroarylalkyl, arylalkenyl, and heteroarylalkenyl.

8. A compound according to claim 7 wherein $R_{18}$, $R_{19}$, and $R_{20}$ are each, independently, hydrogen.

9. A compound according to claim 7 which is selected from the group consisting of:

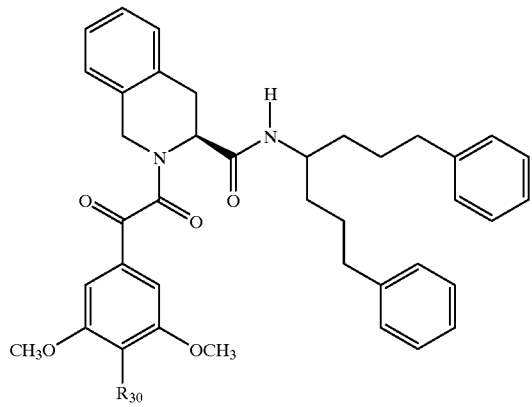

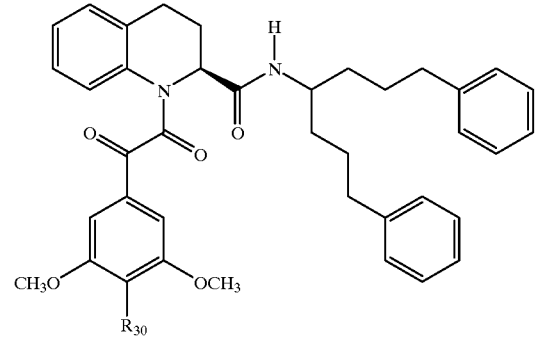

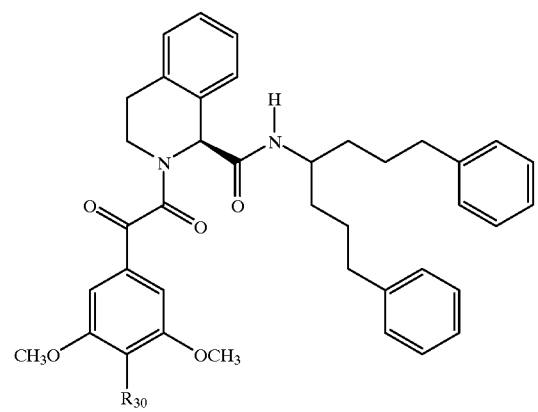

-continued

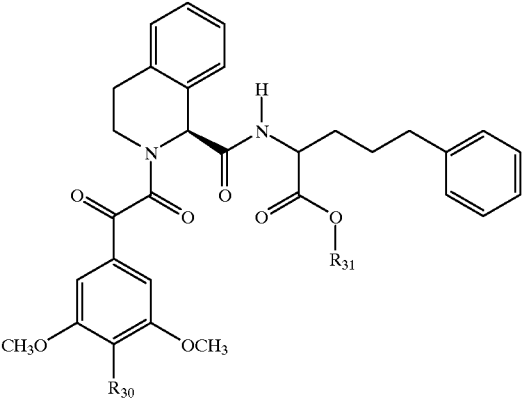

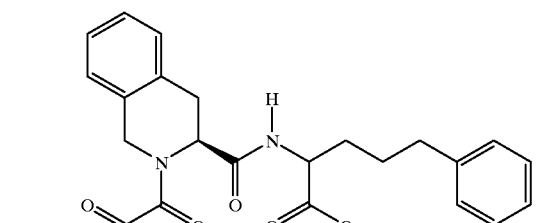

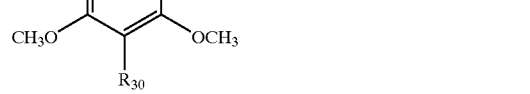

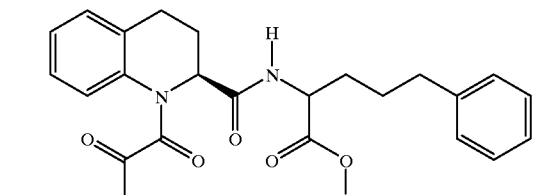

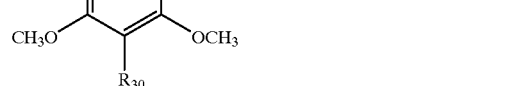

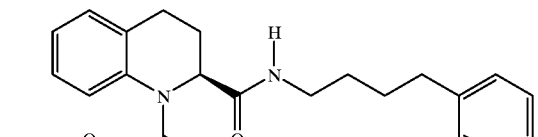

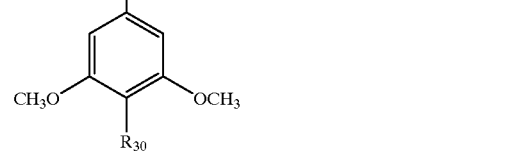

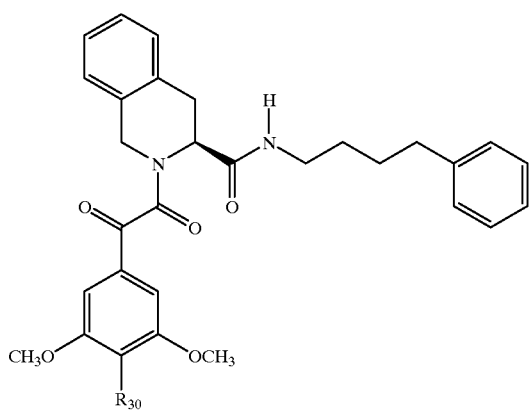
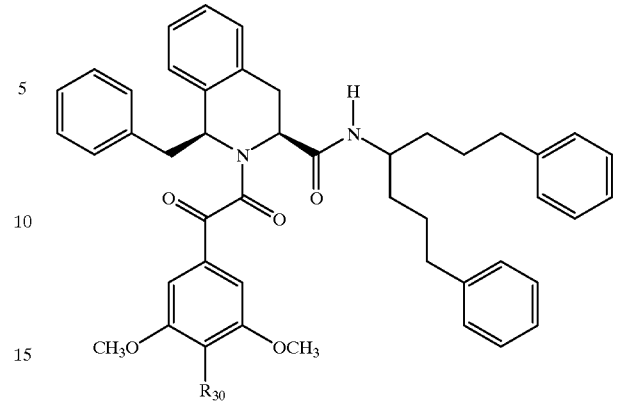
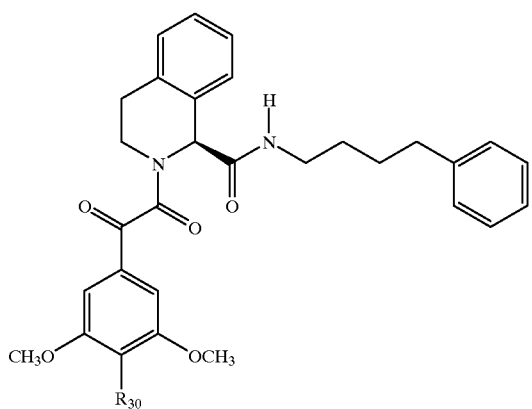
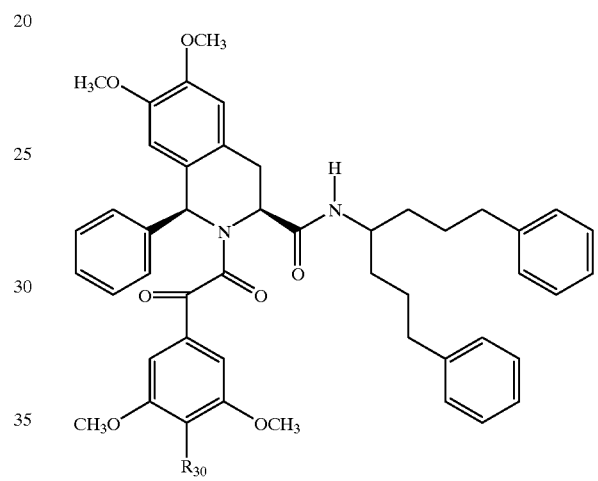
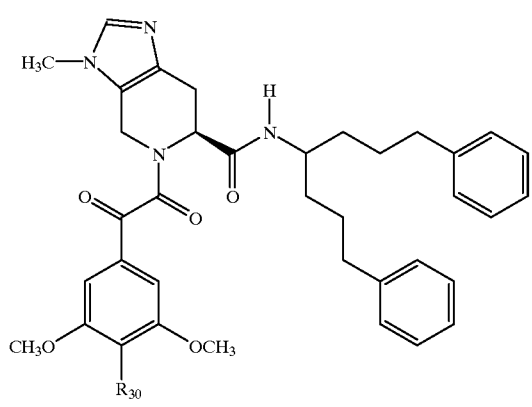
and
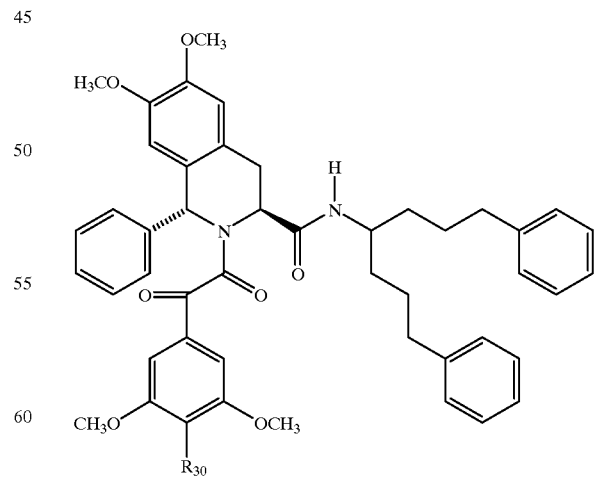

wherein $R_{30}$ is selected from the group consisting of $-OR_{32}$ and $-OCH_2C(O)OR_{32}$, wherein $R_{32}$ is selected from the group consisting of hydrogen and alkyl, and wherein $R_{31}$ is selected from the group consisting of hydrogen, alkyl, heteroalkyl, cycloalkyl, heterocycloalkyl, aryl, heteroaryl, arylalkyl, and heteroarylalkyl.

10. A compound according to claim 9 wherein $R_{30}$ is $-OCH_3$.

11. A composition comprising a compound according to claim 1 and a pharmaceutically-acceptable carrier.

* * * * *